US011141132B2

(12) United States Patent
Wu et al.

(10) Patent No.: US 11,141,132 B2
(45) Date of Patent: Oct. 12, 2021

(54) ULTRASONIC IMAGING DEVICE AND ULTRASONIC IMAGING METHOD USING ULTRASONIC IMAGING DEVICE

(71) Applicant: Hitachi, Ltd., Tokyo (JP)

(72) Inventors: Wenjing Wu, Tokyo (JP); Yushi Tsubota, Tokyo (JP); Kenichi Kawabata, Tokyo (JP); Takahide Terada, Tokyo (JP); Kazuhiro Yamanaka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 442 days.

(21) Appl. No.: 15/762,460

(22) PCT Filed: Jun. 23, 2016

(86) PCT No.: PCT/JP2016/068694
§ 371 (c)(1),
(2) Date: Mar. 22, 2018

(87) PCT Pub. No.: WO2017/221381
PCT Pub. Date: Dec. 28, 2017

(65) Prior Publication Data
US 2018/0271479 A1    Sep. 27, 2018

(51) Int. Cl.
*A61B 8/14* (2006.01)
*A61B 8/15* (2006.01)
(Continued)

(52) U.S. Cl.
CPC .............. *A61B 8/14* (2013.01); *A61B 8/0825* (2013.01); *A61B 8/15* (2013.01); *A61B 8/406* (2013.01);
(Continued)

(58) Field of Classification Search
CPC .......... A61B 8/14; A61B 8/461; A61B 8/406; A61B 8/0825; A61B 8/5207; A61B 8/15;
(Continued)

(56) References Cited

U.S. PATENT DOCUMENTS

| 6,725,076 B1 * | 4/2004 | Jensen | G01P 5/22 367/89 |
| 2011/0201928 A1 * | 8/2011 | Duric | A61B 8/0825 600/438 |
| 2014/0364736 A1 * | 12/2014 | Huang | G01S 15/8997 600/447 |

FOREIGN PATENT DOCUMENTS

| JP | 55-14066 A | 1/1980 |
| JP | 2009-261492 A | 11/2009 |
| JP | 2015-116201 A | 6/2015 |

OTHER PUBLICATIONS

Mohammad Ashfaq, "Measuring and Signal Processing Techniques for Ultrasound Computed Tomography", 2007 (Year: 2007).*
(Continued)

*Primary Examiner* — Pascal M Bui Pho
*Assistant Examiner* — Adil Partap S Virk
(74) *Attorney, Agent, or Firm* — Crowell & Moring LLP

(57) ABSTRACT

According to the present invention, a clear transmitted wave image of a boundary of tissues is generated in a short time. An ultrasonic imaging device of the present invention includes a transducer array in which a plurality of transducers transmitting and receiving an ultrasound wave are arrayed; a transmission unit which delivers an electric signal to at least one of the plurality of transducers, such that the delivered electric signal is converted into an ultrasound wave, and transmits the ultrasound wave to a target; a reception unit which receives a received signal that is an electric signal output by each of the plurality of transducers having received a reflected wave and a transmitted wave of
(Continued)

the ultrasound wave of the target; and an image generation unit which individually generates a reflected wave image of a cross section of the target using a received signal of the reflected wave and a transmitted wave image of the cross section of the target using a received signal of the transmitted wave. The image generation unit includes a reflected wave image boundary detection unit detecting a boundary of the target in the reflected wave image and generating the transmitted wave image such that a boundary in the transmitted wave image corresponding to the boundary detected by the reflected wave image boundary detection unit is emphasized.

8 Claims, 18 Drawing Sheets

(51) Int. Cl.
*A61B 8/00* (2006.01)
*A61B 8/08* (2006.01)
(52) U.S. Cl.
CPC .......... *A61B 8/5207* (2013.01); *A61B 8/4483* (2013.01); *A61B 8/461* (2013.01)
(58) Field of Classification Search
CPC .......... A61B 8/4483; A61B 2034/2063; A61B 2090/378; A61B 2090/3925; A61B 2017/00924; A61B 2017/3413; A61M 25/0108; A61K 49/22
See application file for complete search history.

(56) References Cited

OTHER PUBLICATIONS

Li et al., "In Vivo Breast Sound-speed Imaging with Ultrasound Tomography," Ultrasound in Medicine & Biology 35.10 (2009): p. 1615-1628 (Forty-One (41) pages).
International Search Report (PCT/ISA/210) issued in PCT Application No. PCT/JP2016/068694 dated Aug. 30, 2016 with English-language translation (three (3) pages).
Japanese-language Written Opinion (PCT/ISA/237) issued in PCT Application No. PCT/JP2016/068694 dated Aug. 30, 2016 (three (3) pages).
International Preliminary Report on Patentability (PCT/IB/338 & PCT/IB/373) issued in PCT Application No. PCT/JP2016/068694 dated Jan. 3, 2019, including English translation of document C3 (Japanese-language Written Opinion (PCT/ISA/237) previously filed on Mar. 22, 2018) (six (6) pages).

\* cited by examiner

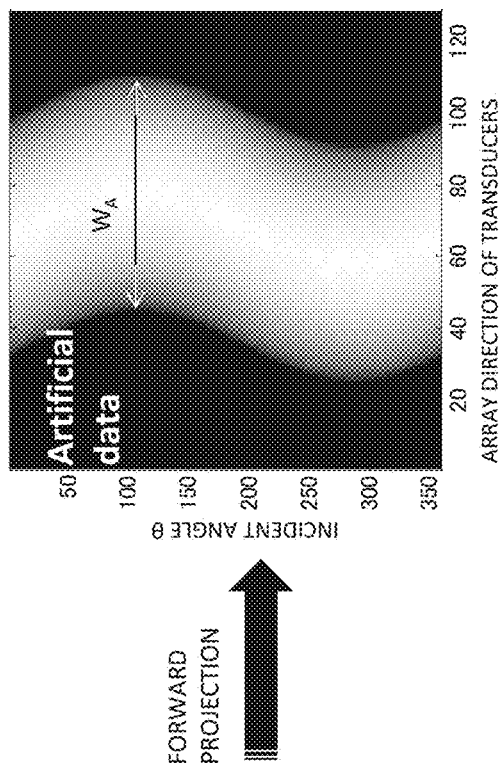
FIG. 5A
FIG. 5B
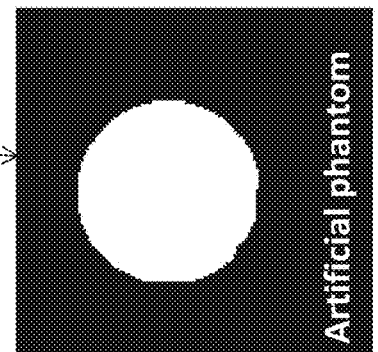
FORWARD PROJECTION
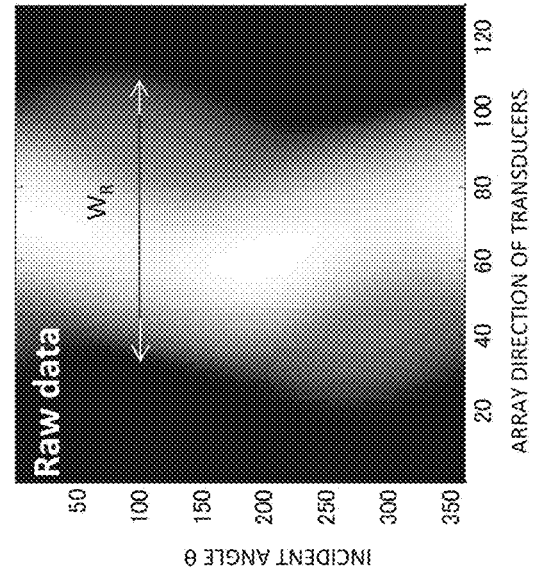
FIG. 5C  Compare  FIG. 5D
ADJUSTMENT
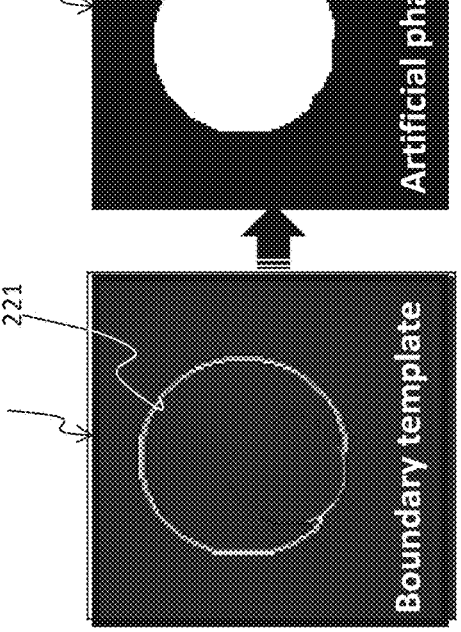
FIG. 5E

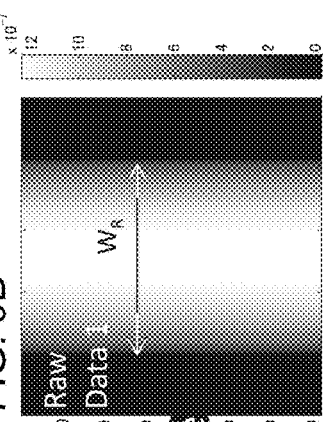
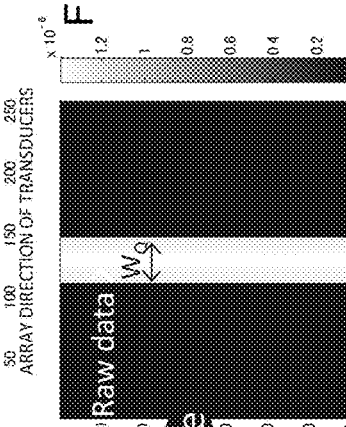
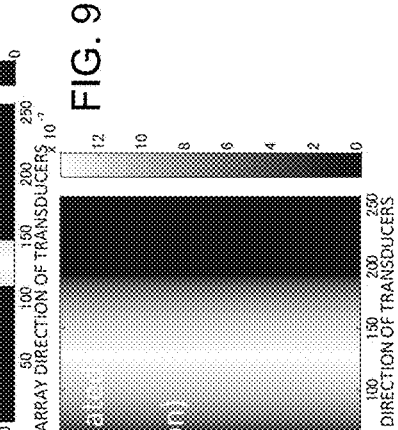
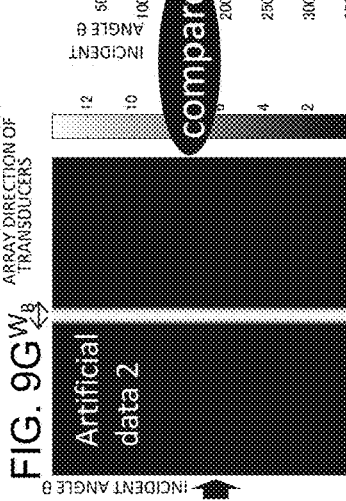
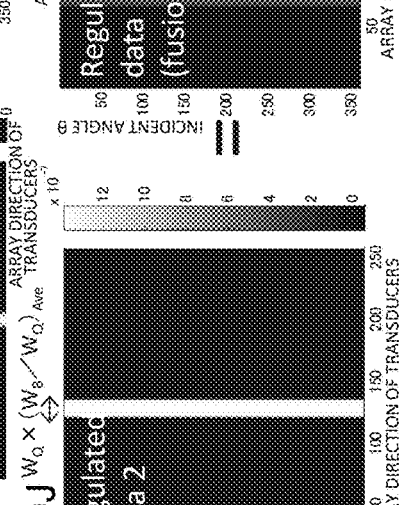
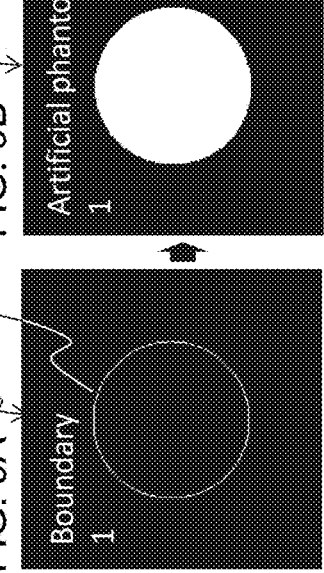
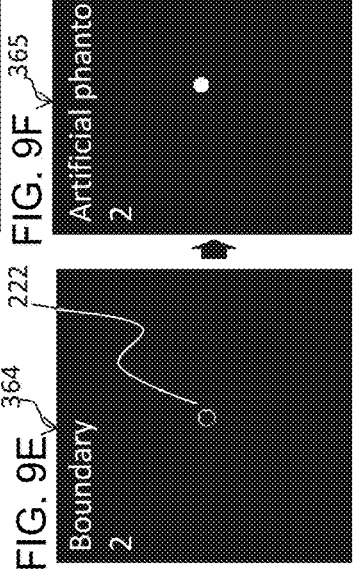
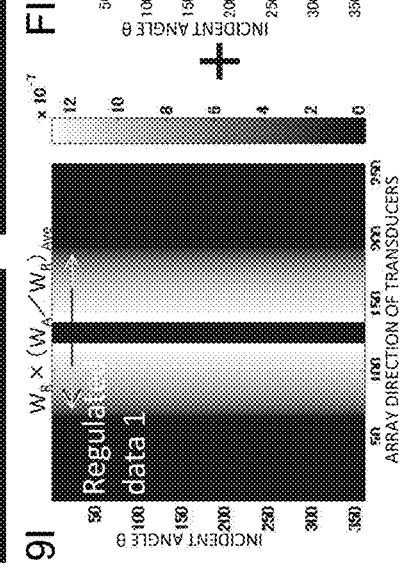

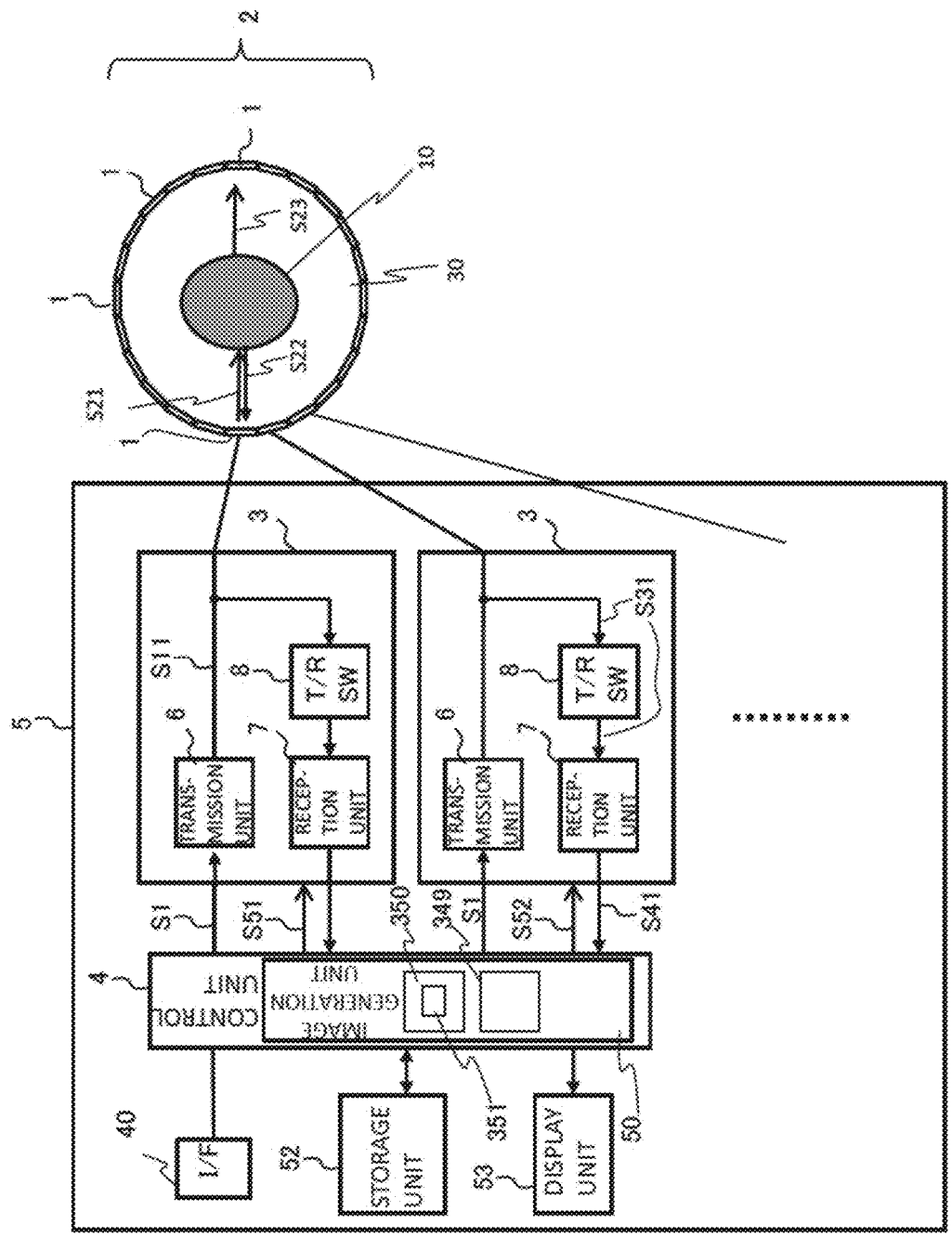

ULTRASONIC IMAGING DEVICE AND ULTRASONIC IMAGING METHOD USING ULTRASONIC IMAGING DEVICE

TECHNICAL FIELD

The present invention relates to an ultrasonic imaging device, particularly relates to an apparatus which generates an image using a reflected wave and a transmitted wave of an ultrasound wave.

BACKGROUND ART

NPL 1 and the like have proposed an ultrasound tomography method in which ultrasound waves are transmitted toward the inside of a target, the ultrasound waves that have passed through the inside of the target in a plurality of paths are individually received, and a sound speed distribution image of a cross section of the target is generated based on a propagation time from the transmission to the reception.

Specifically, in the technology NPL 1, a ring-shaped transducer array is disposed around a cylindrical water tank and breasts are inserted into the water tank. While the ring-shaped transducer array is vertically moved, an ultrasound wave is transmitted in order from each transducer in the transducer array and the ultrasound waves which have penetrated the breasts are received by other transducers. A cross-sectional image of the breasts is reconstructed by calculating a sound speed distribution for each propagation path of an ultrasound wave. In this case, according to NPL 1, the sound speed distribution is calculated considering that a traveling direction of the ultrasound wave is refracted in a boundary of tissues having different densities. Accordingly, compared to a case where the sound speed distribution is calculated on the assumption that an ultrasound wave travels straight forward even in a boundary of tissues, a sound speed distribution image having vivid contours of tissues can be generated, so that accuracy of an image can be improved. In addition, NPL 1 also discloses a method of processing a sound speed distribution image using a threshold value in order to vividly extract contours of predetermined tissues constituting breasts.

CITATION LIST

Patent Literature

[NPL 1] Li, Cuiping, et al. "In vivo breast sound-speed imaging with ultrasound tomography." Ultrasound in medicine & biology 35.10 (2009): 1615-1628.

SUMMARY OF INVENTION

Technical Problem

As in NPL 1, in a method of calculating a sound speed distribution considering that an ultrasound wave is refracted in a boundary of tissues having different densities, in a case where structures of tissues or densities thereof within a target are unknown, it is not possible to ascertain the way of preferably assuming the position and the angle of refraction and calculating a propagation path of an ultrasound wave. Therefore, based on various assumptions, there is a need to employ a method of setting a refracted propagation path, a method of setting a propagation path of an ultrasound wave by acquiring a sound speed distribution image first through any technique, searching for a boundary in which the sound speed changes in the image, and obtaining a refraction angle of an ultrasound wave based on differences in the sound speed, or the like. All of the methods require a time for a calculation in order to set a refracted propagation path and also require a time for recalculating the sound speed distribution using the set propagation path. Therefore, a calculation amount increases and the time for generating an image is lengthened.

An object of the present invention is to generate a clear transmitted wave image of a boundary of tissues in a short time.

Solution to Problem

In order to solve the problem, the present invention includes a transducer array in which a plurality of transducers transmitting and receiving an ultrasound wave are arrayed; a transmission unit which delivers an electric signal to at least one of the plurality of transducers, such that the delivered electric signal is converted into an ultrasound wave and the ultrasound wave is transmitted to a target; a reception unit which receives a received signal that is an electric signal output by each of the plurality of transducers having received at least one of a reflected wave and a transmitted wave of the ultrasound wave of the target; and an image generation unit which individually generates a reflected wave image of a cross section of the target using a received signal of the reflected wave and a transmitted wave image of the cross section of the target using a received signal of the transmitted wave. The image generation unit includes a reflected wave image boundary detection unit detecting a boundary of the target in the reflected wave image and the image generation unit generates the transmitted wave image such that a boundary in the transmitted wave image corresponding to the boundary detected by the reflected wave image boundary detection unit is emphasized.

Advantageous Effects of Invention

According to the present invention, a clear transmitted wave image of a boundary of tissues can be generated in a short time.

BRIEF DESCRIPTION OF DRAWINGS

FIGS. 5A to 5E are views illustrating an operation of a received signal adjustment unit of Embodiment 1.

FIGS. 9A to 9K are views illustrating an operation of a received signal adjustment unit and a second received signal adjustment unit of Embodiment 2.

FIG. 10 is a block diagram illustrating an overall configuration of an ultrasonic imaging device of Embodiment 3.

DESCRIPTION OF EMBODIMENTS

Embodiments of the present invention will be described using the drawings.

Embodiment 1

An ultrasonic imaging device of Embodiment 1 will be described.

Figure 1:
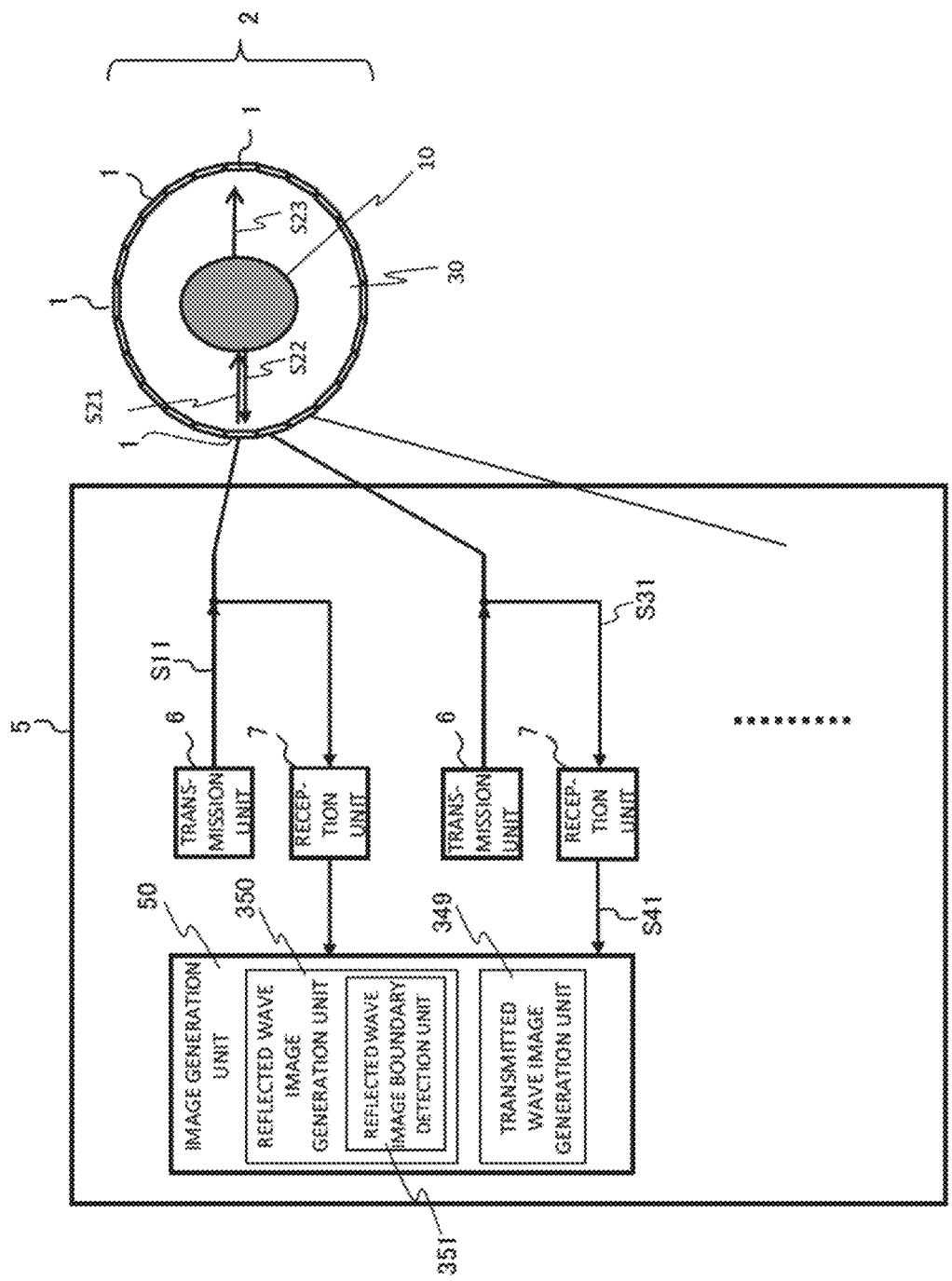
FIG. 1 is a block diagram illustrating an overall configuration of an ultrasonic imaging device of Embodiment 1.
Figure 2:
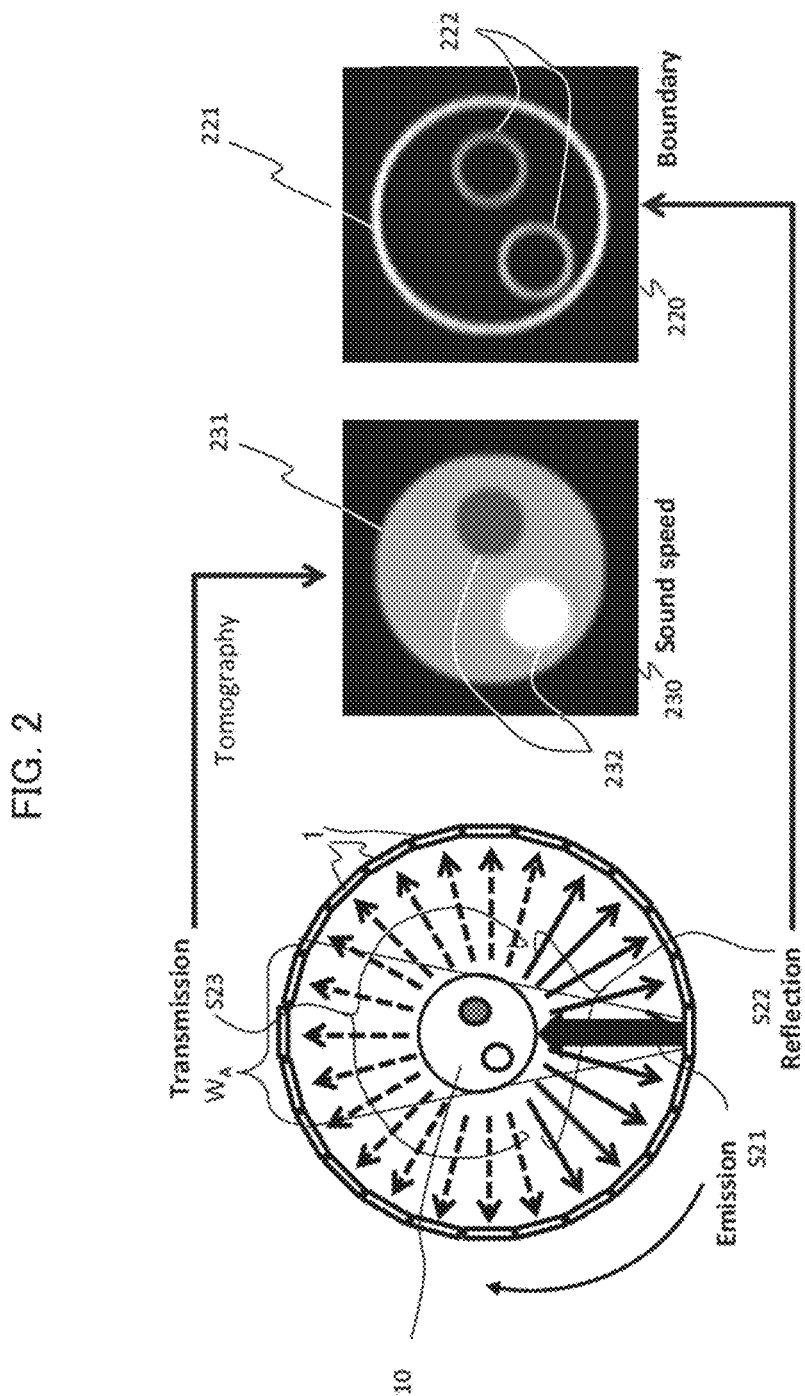
FIG. 2 is a view illustrating a reflected wave and a transmitted wave of an ultrasound wave of a target, and a reflected wave image and a transmitted wave image generated by using a received signal thereof.

FIG. 1 is a block diagram illustrating an overall configuration of the apparatus. FIG. 2 is a view illustrating a reflected wave and a transmitted wave of an ultrasound wave of a target, and a reflected wave image and a transmitted wave image generated by using a received signal thereof. The ultrasonic imaging device of the present embodiment includes a transducer array 2 in which a plurality of transducers 1 transmitting and receiving an ultrasound wave are arrayed, a transmission unit 6, a reception unit 7, and an image generation unit 50. The transmission unit 6 delivers an electric signal S11 to at least one of the plurality of transducers 1, such that the delivered electric signal S11 is converted into an ultrasound wave S21, and transmits the ultrasound wave S21 to a target 10. The plurality of transducers 1 individually receive at least one of a reflected wave S22 and a transmitted wave S23 of the ultrasound wave S21 of the target 10 and output a received signal S31 which is an electric signal. The reception unit 7 receives the received signal S31 from the transducer 1 and delivers the received signal S31 to the image generation unit 50. The image generation unit 50 includes a reflected wave image generation unit 350 and a transmitted wave image generation unit 349. The reflected wave image generation unit 350 generates a reflected wave image 220 of a cross section of the target 10 using the received signal S31 of the reflected wave S22 received from the reception unit 7. The transmitted wave image generation unit 349 generates a transmitted wave image 230 of the cross section of the target 10 using the received signal S31 of the transmitted wave S23 received from the reception unit 7. The image generation unit 50 further includes a reflected wave image boundary detection unit 351, thereby detecting a boundary 221 of the target 10 in the reflected wave image 220. The transmitted wave image generation unit 349 generates the transmitted wave image 230 such that a boundary 231 in the transmitted wave image 230 corresponding to the boundary 221 detected by the reflected wave image boundary detection unit 351 is emphasized.

In a case where there is also a boundary (for example, a boundary 222) within the target 10, the reflected wave image boundary detection unit 351 may detect the boundary 221 and detect the boundary 222. In this case, the transmitted wave image generation unit 349 generates the transmitted wave image 230 such that a boundary 232 in the transmitted wave image 230 corresponding to the boundary 222 is emphasized.

In this manner, in the present embodiment, the boundary 221 is detected in the reflected wave image 220 utilizing that a clear image of the boundary of the target 10 is more likely to be acquired in the reflected wave image 220 than the transmitted wave image 230, and an image is generated such that the corresponding boundary 231 in the transmitted wave image 230 becomes clear. Accordingly, compared to a case where image processing or the like is performed with only the transmitted wave image 230, it is possible to achieve an effect that a transmitted wave image 230 having a clear boundary can be generated in a short time.

The examples of FIGS. 1 and 2 illustrate the transducer array 2 having a ring shape in which the plurality of transducers 1 are disposed to surround the target 10. However, the shape thereof is not limited to this shape. Any shape and disposition may be used as long as the transducer array can irradiate the target 10 with the ultrasound wave S21 and can receive the reflected wave S22 and the transmitted wave S23 thereof. For example, it is possible to use a pair of linear or curved transducer arrays disposed to face each other.

Any image may be used as the transmitted wave image 230 as long as the image can be reconstructed based on information of the transmitted wave S23. For example, as the transmitted wave image 230, the transmitted wave image generation unit 349 generates a sound speed distribution image within the target 10 or an ultrasound attenuation rate distribution image (or an ultrasound wave attenuation amount distribution image) within the target 10.

Figure 3:
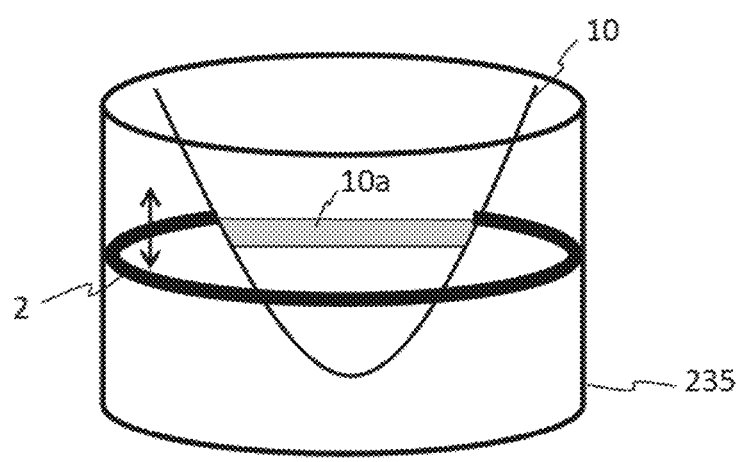
FIG. 3 is a perspective view illustrating a positional relationship between a transducer array and a target 10 of Embodiment 1.

In addition, it is desirable that the target 10 is immersed in a substance (for example, water) which causes small attenuation of the ultrasound wave S21 and on which the ultrasound wave S21 emitted from the transducer 1 can be incident with a low loss. For example, as in FIG. 3, it is preferable that the transducer array 2 is disposed inside a water tank 235 filled with water, the target 10 is inserted into the water tank 235, and ultrasound waves are thereby transmitted and received. Due to this configuration, the transducer array 2 is vertically moved inside the water tank 235, and the reflected wave image 220 and the transmitted wave image 230 of a desired cross section 10a of the target 10 are captured.

Figure 4:
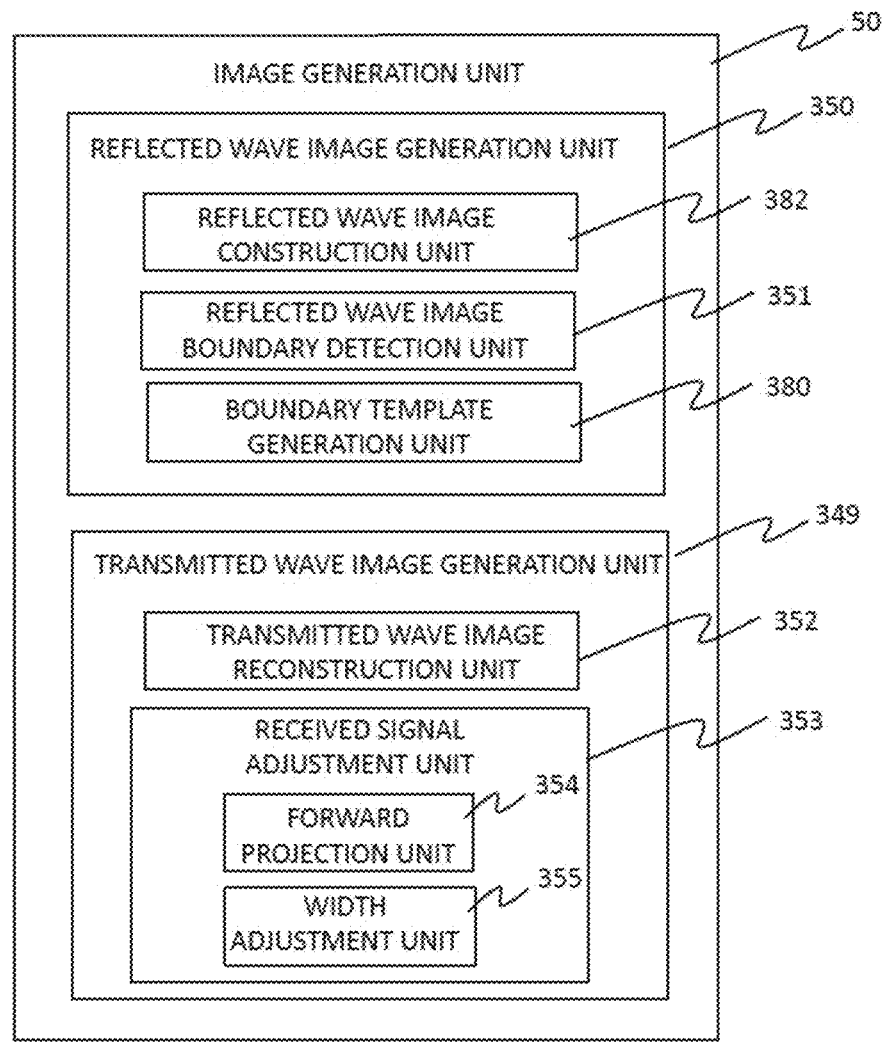
FIG. 4 is a functional block diagram of an image generation unit of Embodiment 1.

Hereinafter, configurations of the reflected wave image generation unit 350 and the transmitted wave image generation unit 349 will be described in detail using a functional block diagram in FIG. 4. The reflected wave image generation unit 350 has a reflected wave image construction unit 382 which generates the reflected wave image 220 based on the reflected wave S22 of the ultrasound wave S21, the reflected wave image boundary detection unit 351 which detects the boundary of the target 10 (for example, the boundary between water and the target 10 or the boundary between tissues within the target 10) in the reflected wave image 220, and a boundary template generation unit 380 which generates a boundary template based on the detected boundary. In addition, the transmitted wave image generation unit 349 has a transmitted wave image reconstruction unit 352 which reconstructs the transmitted wave image 230 through an ultrasound tomography method, and a received signal adjustment unit 353 which adjusts a received signal of the transmitted wave S23 to be used by the transmitted wave image reconstruction unit 352 in reconstruction in order to emphasize the image of the boundary 231 in the transmitted wave image 230.

The transmission unit 6 irradiates the target 10 with the ultrasound wave S21 from the transducer 1. The reflected wave S22 and the transmitted wave S23 of the ultrasound wave S21 are received by the transducer 1 and are received by the reception unit 7. The reflected wave image construction unit 382 of the reflected wave image generation unit 350 generates the reflected wave image 220 using a received signal of the reflected wave S22. The transmitted wave image reconstruction unit 352 of the transmitted wave image generation unit 349 reconstructs the transmitted wave image 230 through the ultrasound tomography method using a received signal of the transmitted wave S23. In order to make this possible, the transmission unit 6 transmits the ultrasound wave S21 having a predetermined spreading angle a plurality of times by changing the position of the transducer 1 transmitting the ultrasound wave S21, while changing the incident angle of the ultrasound wave on the target 10. The reception unit 7 receives received signals of the reflected wave S22 and the transmitted wave S23 of the ultrasound wave of the target 10 every time the ultrasound wave S21 is transmitted.

In this case, as illustrated in FIG. 2, the reception unit 7 may receive a received signal of the transmitted wave S23 using the transducer 1 positioned in a predetermined angle range with respect to the transducer 1 which has transmitted the ultrasound wave S21 and may receive the reflected wave S22 using the transducer 1 positioned in a different predetermined angle range. In addition, the reception unit 7 may receive received signals of all of the transducers 1. In such a case, depending on the position of the transducer 1, both the transmitted wave S23 and the reflected wave S22 arrive and received signals of both thereof are output. However, both thereof have different propagation paths for arriving at the receiving transducer 1 from the transmitting transducer 1, thereby having different arrival time zones. Thus, in accordance with a positional relationship between the transducer 1 which has transmitted the ultrasound wave S21 and the receiving transducer 1, the image generation unit 50 individually extracts a received signal of the transmitted wave S23 and a received signal of the reflected wave S22 by extracting received signals in the time zone set in advance, thereby using the extracted received signals for generating an image.

The reflected wave image construction unit 382 of the reflected wave image generation unit 350 extracts a received signal of the reflected wave S22 from the received received signal of the ultrasound wave and generates the reflected wave image 220 based on the received signal of the reflected wave S22. As a method of generating the reflected wave image 220 performed by the reflected wave image construction unit 382, a known generating method can be used. As an example, the reflected wave image construction unit 382 calculates a signal delay time which is a difference between a timing (time) at which the ultrasound wave signal S21 is transmitted and a timing (time) at which the extracted received signal of the reflected wave S22 is received. The reflected wave image construction unit 382 multiplies the signal delay time by a sound speed set in advance and obtains the distance of the propagation path between the transducer 1 which has transmitted an ultrasound wave and the receiving transducer 1. The reflected wave image construction unit 382 calculates the position of a reflection point, at which the ultrasound wave signal S21 is reflected, based on the distance thereof. Then, the reflected wave image construction unit 382 generates the reflected wave image 220 by converting amplitude of the received signal of the reflected wave S22 into luminance and setting the luminance of the position (pixel) of the reflection point thereof.

Meanwhile, the transmitted wave image reconstruction unit 352 of the transmitted wave image generation unit 349 reconstructs the transmitted wave image 230 by performing a computation for causing the received signal of the transmitted wave S23 to be subjected to back projection in in a space where the target 10 is disposed.

The reflected wave image boundary detection unit 351 detects the boundary 221 and the like of the target 10 by performing image processing set in advance with respect to the reflected wave image 220. The image processing need only be able to detect a boundary. For example, binary coded processing, mask processing, or filter processing is used.

The boundary template generation unit 380 of the reflected wave image generation unit 350 extracts the shape of the boundary 221 which is an outside boundary (on the outer side) among the boundaries detected by the reflected wave image boundary detection unit 351, Accordingly, as illustrated in FIG. 5(a), a template (boundary template) 356 corresponding to the boundary 221 is generated, and the template 356 is transmitted to the transmitted wave image generation unit 349. Here, the boundary template is a template (reflected wave information template) based on information acquired from the reflected wave. The boundary template generation unit 380 also serves as a reflected wave information template generation unit.

The received signal adjustment unit 353 of the transmitted wave image generation unit 349 emphasizes an image of the boundary 231 in the transmitted wave image 230 reconstructed by processing a received signal of the transmitted wave S23 to be used by the transmitted wave image reconstruction unit 352 in reconstruction. Therefore, as illustrated in FIG. 4, the received signal adjustment unit 353 includes a forward projection unit 354 and a width adjustment unit 355.

The forward projection unit 354 of the transmitted wave image generation unit 349 generates an artificial phantom 381 (refer to FIG. 5(b)) having a shape of the template 356, based on the template 356 received from the boundary template generation unit 380 of the reflected wave image generation unit 350.

Here, an artificial phantom is a phantom related to a sound speed or attenuation which is information acquired from the transmitted wave and is a template (transmitted wave information template) based on information acquired from a transmitted wave. For example, in a case where an image related to a sound speed is generated as a transmitted wave image, the forward projection unit 354 of the transmitted wave image generation unit 349 generates an artificial phantom (sound speed template) having information of a sound speed. In addition, in a case where an image related to attenuation is generated as a transmitted wave image, the forward projection unit 354 of the transmitted wave image generation unit 349 generates an artificial phantom (attenuation template) having information of attenuation. In addition, the forward projection unit 354 also serves as a transmitted wave information phantom generation unit.

For example, in the artificial phantom 381, the ultrasound attenuation rate of the inner region of the boundary 221 is a value A1 set in advance, and the ultrasound attenuation rate of the outer region of the boundary 221 is a value A2 (>A1, for example, A2 is infinite) set in advance.

Moreover, through a computation, the forward projection unit 354 obtains the intensity of a received signal acquired in a case where the artificial phantom 381 is subjected to forward projection in the transducer array 2. For example, through a computation, the forward projection unit 354 obtains a range $W_A$ (refer to FIG. 2) of the transducer 1 for receiving the transmitted wave S23 which has penetrated straight the phantom 381 in a case where the ultrasound wave S21 is transmitted to the artificial phantom 381 under the same condition as when the received signal for generating the transmitted wave image 230 is received. The intensity of a received signal of the transducer 1 in the range is $W_A$ a predetermined value, and the intensity of received signals of other transducers 1 is another predetermined value (for example, zero) (refer to FIG. 5(c)). This computation is repeated by changing the transducer 1 for transmitting the ultrasound wave S21 while changing an incident angle θ on the target 10 in the same manner as when the received signal for generating the transmitted wave image 230 is received. The range $W_A$ of a transducer, which has been obtained for each incident angle θ, for receiving the transmitted wave S23 can be expressed in a sinogram having an array direction of the transducers 1 and the incident angle θ of the ultrasound wave S21 on the target 10 at the time of transmission as axes, for example, as is FIG. 5(c). The range $W_A$ of a transducer, at which the transmitted wave S23 having penetrated straight the inner side of the phantom 381 corresponding to the shape of the boundary 221 arrives, is expressed as a belt-like region of white (in which the received signal has a predetermined value) belt-like region, and the range of the transducer 1, at which the transmitted wave S23 having penetrated the outer region of the phantom 381 arrives (or no transmitted wave S23 arrives), is expressed in black (in which the received signal is zero).

The width adjustment unit 355 adjusts a spreading width $W_R$ in the array direction of the transducers 1 for an actual received signal to be used for generating the transmitted wave image 230 (refer to FIG. 5(d)) such that the spreading width $W_R$ approximates the range $W_A$ of the transducer 1 obtained by the forward projection unit 354. The spreading width $W_R$ in the array direction of the transducers for an actual received signal to be used for generating the transmitted wave image 230 can be expressed in a sinogram as in FIG. 5(d). The range $W_R$ of the transducer 1, at which the transmitted wave S23 having penetrated the inner side of the target 10 arrives, is expressed as a white belt-like region. The depth of (luminance) of the white part in the belt-like region indicates the intensity of the received signal (amplitude). The region of the transducer 1 at which no transmitted wave S23 has arrived is expressed in black, and it is possible to known that the intensity of the received signal of the transmitted wave S23 is zero. The width adjustment unit 355 widens or reduces the range $W_R$ of the actual received signal so that the range $W_R$ thereof approximates the range $W_A$ obtained from the template 356 corresponding to the boundary 221 of the reflected wave image 220. For example, the width adjustment unit 355 obtains a ratio $W_A/W_R$ of the range $W_A$ to the range $W_R$ for each incident angle θ of the ultrasound wave S21 and calculates an average $(W_A/W_R)_{Ave}$ of the obtained ratios $W_A/W_R$. The width adjustment unit 355 performs an adjustment in which the spreading width $W_R$ is widened or reduced to approximate the range $W_A$, by applying the obtained average $(W_A/W_R)_{Ave}$ to the value of the range $W_R$ of the transducers 1 in the entire belt-like region of the sinogram in FIG. 5(d). FIG. 5(e) illustrates a received signal after being adjusted by the width adjustment unit 355.

Figure 7A:
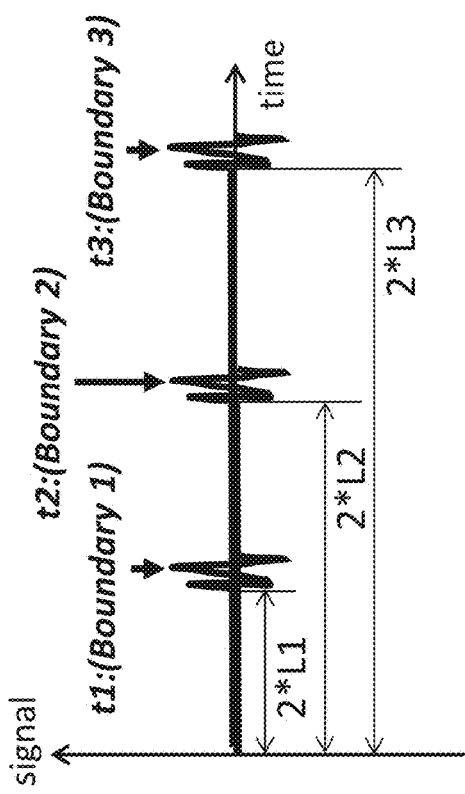
FIGS. 7A to 7C are views illustrating a procedure of generating a post-adjustment reflected wave image from a post-adjustment transmitted wave image.

The transmitted wave image reconstruction unit 352 reconstructs a post-adjustment transmitted wave image 233 (refer to FIG. 7(a)) by performing back projection of a received signal after being adjusted by the width adjustment unit 355 (FIG. 5(e)).

In this manner, the spreading width $W_R$ of an actual received signal in the array direction of the transducers 1 is caused to coincide with the range $W_A$ obtained from the template 356 corresponding to the boundary 221 of the reflected wave image 220, so that it is possible to eliminate or reduce the influence of scattering from the detected received signal which spreads outward by scattering within the target 10. Thus, the phenomenon in which the boundary 231 of the transmitted wave image 230 spreads and becomes unclear due to the influence of scattering is suppressed, and the post-adjustment transmitted wave image 233 having the emphasized boundary 231 is reconstructed.

In this manner, since the received signal adjustment unit 353 adjusts the spreading width $W_R$ of an actual received signal in the array direction of the transducers 1, it is possible to generate the post-adjustment transmitted wave image 233 in which the boundary 231 corresponding to the boundary 221 of the reflected wave image 220 is emphasized in the transmitted wave image 230, during the process of reconstructing the transmitted wave image 230.

As described above, in the ultrasonic imaging device of Embodiment 1, since the post-adjustment transmitted wave image 233 in which the boundary 231 corresponding to the boundary 221 of the reflected wave image 220 is emphasized can foe generated during the process of reconstructing the transmitted wave image 230, it is possible to generate a transmitted wave image having a clear boundary of tissues in a short time.

Embodiment 2

An ultrasonic imaging device of Embodiment 2 will be described. In addition to the configuration of the ultrasonic imaging device of Embodiment 1, the ultrasonic imaging device of Embodiment 2 has a function of generating a reflected wave image (which will hereinafter be referred to as a post-adjustment reflected wave image 223) through a computation using the post-adjustment transmitted wave image 233 in which the boundary 231 generated by the ultrasonic imaging device of Embodiment 1 is emphasized. Moreover, the ultrasonic imaging device of Embodiment 2 also has a function of additionally generating a transmitted wave image in which a boundary different from the boundary 231, for example, the boundary 232 positioned on an inner side than the boundary 231 is emphasized, by using the post-adjustment reflected wave image 223. A configuration of the image generation unit 50 of the ultrasonic imaging device of Embodiment 2 having the functions will be described. The ultrasonic imaging device of Embodiment 2 is based on the premise that the apparatus has a configuration similar to that of the ultrasonic imaging device of Embodiment 1. Description will be omitted for the configuration similar to that of the apparatus of Embodiment 1, and only different configurations will be described.

Figure 6:
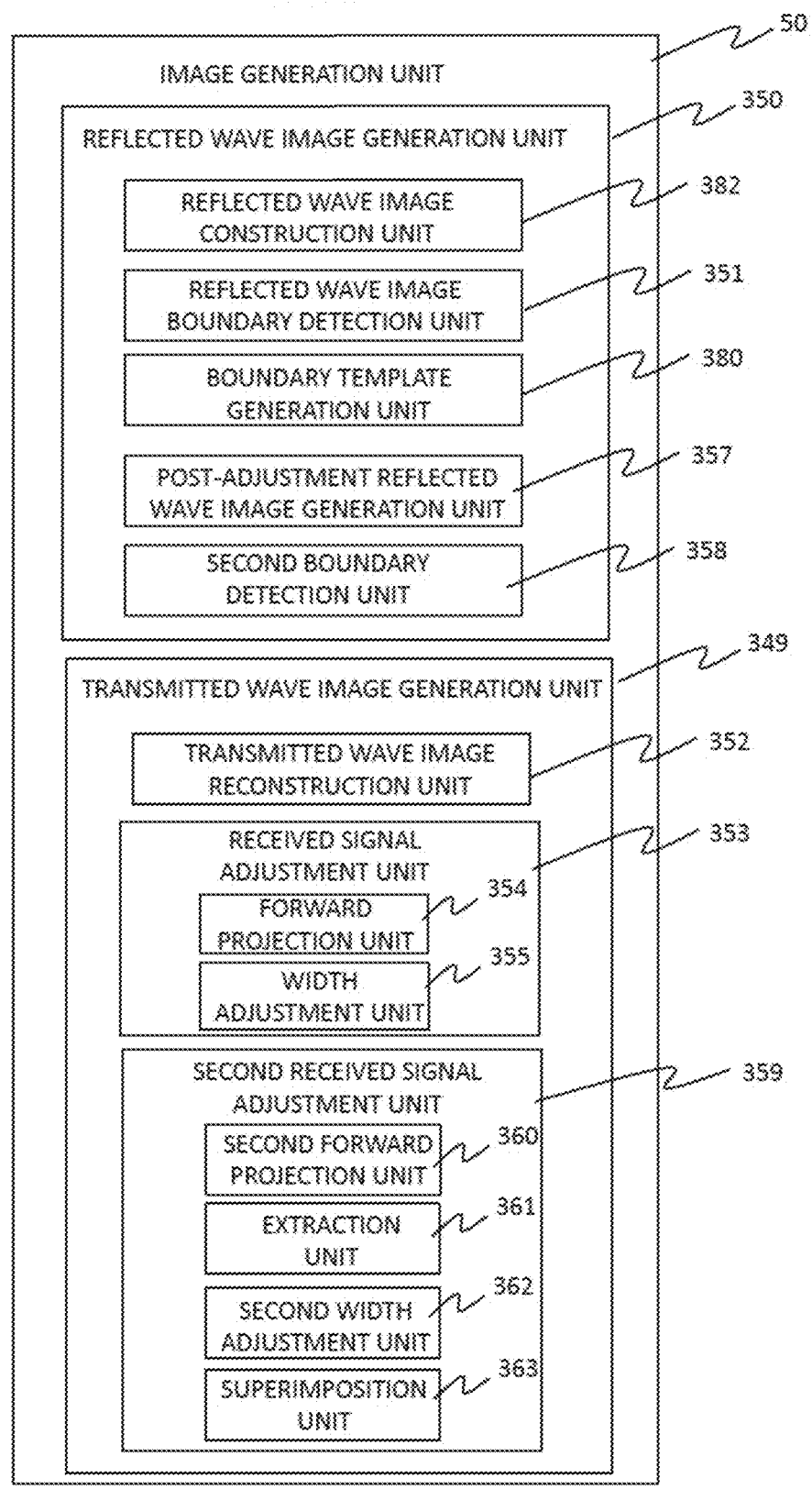
FIG. 6 is a functional block diagram of an image generation unit of Embodiment 2.

As illustrated in FIG. 6, in addition to the configuration described in Embodiment 1, the image generation unit 50 further includes a post-adjustment reflected wave image generation unit 357 and a second boundary detection unit 358 inside the reflected wave image generation unit 350. The image generation unit 50 further includes a second received signal adjustment unit 359 inside the transmitted wave image generation unit 349.

Through a computation, the post-adjustment reflected wave image generation unit 357 generates the post-adjustment reflected wave image 223 acquired in a case where an ultrasound wave is transmitted to an artificial phantom having a distribution of ultrasound penetration characteristics expressed in the post-adjustment transmitted wave image 233, using the post-adjustment transmitted wave image 233 in which the boundary 231 transmitted from the transmitted wave image generation unit 349 is emphasized (FIG. 7(a)), and the reflected wave S22 thereof is received. For example, as illustrated in FIG. 7(a), it is assumed that an ultrasound wave emitted from the transducer 1 in a direction orthogonal to the transducer array 2 is propagated at a sound speed c in the distribution of ultrasound penetration characteristics indicated in an ultrasound penetration characteristic image which is the post-adjustment transmitted wave image 233, the ultrasound wave is reflected by the boundary 231 of two regions having different ultrasound penetration characteristics, and the reflected wave S22 arrives at the transducer 1 again and is received by the transducer 1. In addition, it is possible to assume that a portion of the ultrasound wave passes through the boundary 231 and is reflected by the next boundary 232, and the reflected wave S22 arrives at the transducer 1 again and is received by the transducer 1. In addition, it is possible to assume that a portion of the ultrasound wave passes through the boundary 232 and is reflected by the next boundary 232, and the reflected wave S22 arrives at the transducer 1 again and is received by the transducer 1.

Figure 7B:
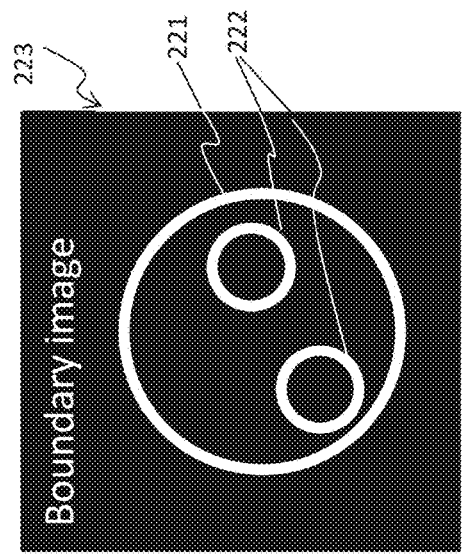

FIG. 7(b) is a view illustrating a time t at which an ultrasound wave transmitted from a certain transducer 1 is propagated in each of the regions (the outer region of the boundary 231, the region between the boundaries 231 and 232, the inner region of the boundary 232) in the post-adjustment transmitted wave image 233 with ultrasound penetration characteristics (sound speed) indicated in the image, is reflected by each of the boundaries of the regions having different sound speeds, and arrives at the transducer array 2 as a received signal of the reflected wave. In the transducer array 2, a received signal of a reflected wave, that is, an ultrasound wave, which has been transmitted from the transducer 1 and is reflected by the boundary 231, is received at a time t1 (boundary 1). A received signal of a reflected wave, that is, the ultrasound wave, which has passed through the boundary 231 and is reflected by the next boundary 232, is received at a time t2 (boundary 2). A received signal of a reflected wave, that is, the ultrasound wave, which has passed through the boundary 232 and is reflected by the next boundary 232, is received at a time t3 (boundary 3).

The post-adjustment reflected wave image generation unit 357 calculates a distance L between the transducer 1 of the transducer array 2 which is artificially disposed and the boundary of the distribution of ultrasound penetration characteristics, through the following Expression (1) using the distribution of ultrasound penetration characteristics (sound speed $c_{variable}$) which is indicated in the post-adjustment transmitted wave image 233 of the target 10, and the time t at which the received signal of the reflected wave reflected by each of the boundaries is received.

$$2L = t \cdot c_{variable} \quad (1)$$

For example, the post-adjustment reflected wave image generation unit 357 calculates a distance L1 between the transducer 1 and the boundary 231, a distance L2 between the transducer 1 and the boundary 232 positioned on the front side when seen from the transducer 1, and a distance L3 between the transducer 1 and the boundary 232 positioned on the rear side when seen from the transducer 1, through a computation.

Figure 7C:
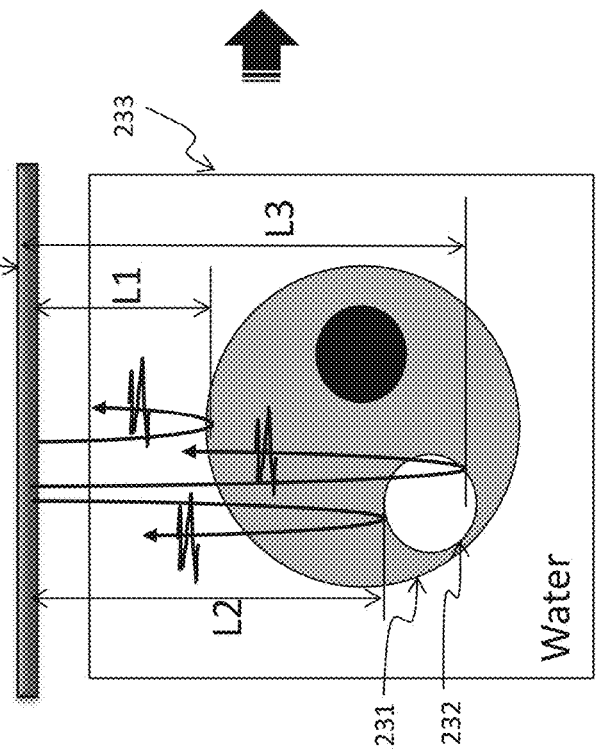

The post-adjustment reflected wave image generation unit 357 performs a computation of Expression (1) described above with respect to each of the transducers 1 and calculates each of the distances L between the boundaries 231 and 232 at positions respectively facing the transducers 1 and the transducers 1 through a computation. The post-adjustment reflected wave image generation unit 357 plots each of the calculated distances L for each transducer 1, thereby generating the post-adjustment reflected wave image 223, as in FIG. 7(c). Accordingly, the post-adjustment reflected wave image 223 is generated from the post-adjustment transmitted wave image 233 through a computation. In the post-adjustment reflected wave image 223, the boundary 221 is emphasized and expressed to be clearer than that in the reflected wave image 220 generated by the reflected wave image generation unit 350, and the boundary 222 positioned on the inner side than the boundary 221 is also expressed to be clearer than that in the reflected wave image 220.

Figure 8:
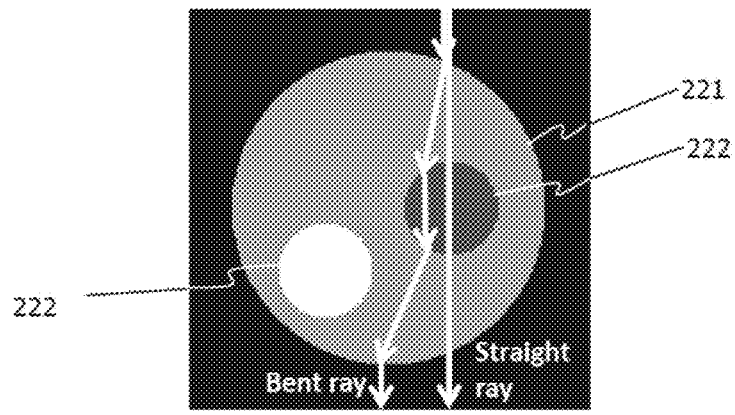
FIG. 8 is a view illustrating refraction of an ultrasound wave propagation path within a phantom corresponding to a transmitted wave image.

FIG. 7(a) illustrates an example in which the post-adjustment reflected wave image generation unit 357 sets the propagation path such that an ultrasound wave travels straight forward to the boundary of the distribution of ultrasound penetration characteristics called a straight ray model. However, as in FIG. 8, the propagation path may be set while considering that an ultrasound wave is refracted in accordance with a difference in ultrasound penetration characteristics in the boundaries 221 and 222 of the regions having different ultrasound penetration characteristics called a bent ray model. In this case, in the example of FIG. 7(a), the post-adjustment reflected wave image generation unit 357 obtains an angle $\phi$ of refraction of an ultrasound wave in the boundaries 231 and 232 of the regions having different ultrasound penetration characteristics through a computation using Snell's law or the like. The post-adjustment reflected wave image generation unit 357 sets the propagation path of an ultrasound wave in accordance with the refraction angle $\phi$ and calculates the time t at which an ultrasound wave emitted from the transducer 1 passes through the first boundary 231 while being refracted, is reflected by the next boundary 232, and arrives at the transducer array 2. The distance L between the transducer 1 and the boundary 232 is calculated based on the refracted propagation path and the time t, and the post-adjustment reflected wave image 223 is generated.

FIGS. 9(a) to 9(d) are views corresponding to FIGS. 5(a) to 5(d) and illustrating operations of the boundary template generation unit 380 of the reflected wave image generation unit 350 and the received signal adjustment unit 353 of the transmitted wave image generation unit 349. FIGS. 9(e) to 9(k) are views illustrating a second template 364 acquired through an operation of the boundary template generation unit 380 of the reflected wave image generation unit 350, and a second phantom 365 and examples of images acquired through an operation of the second received signal adjustment unit 359.

The second boundary detection unit 358 detects the boundary 221 corresponding to the boundary 231 in the post-adjustment reflected wave image 223 and further detects the second boundary 222 positioned on the inner side of the detected boundary 221. The boundary template generation unit 380 extracts the shape of the boundary 222 which is an inner boundary (on the inner side) among the boundaries detected by the second boundary detection unit 358. The boundary template generation unit 380 generates a template 364 corresponding to the boundary 222 as in FIG. 9(e) and transmits the generated template 364 to the transmitted wave image generation unit 349.

The second received signal adjustment unit 353 generates an artificial phantom 365 having a shape of the template 364 based on the transmitted template 364 as in FIG. 9(f) and adjusts the post-adjustment transmitted wave image 233 such that the second boundary 222 is emphasized in the post-adjustment transmitted wave image 233. Therefore, the second received signal adjustment unit 359 includes a second forward projection unit 360, an extraction unit 361, a second width adjustment unit 362, and a superimposition unit 363. Hereinafter, functions of the second forward projection unit 360 and the like will be described.

The second forward projection unit 360 generates the artificial second phantom 365 (FIG. 9(f)) having the shape of the second template 364, based on the received second template 364 and performs a computation for causing the artificial second phantom 365 to be subjected to forward projection in the transducer array 2. Specifically, the second forward projection unit 360 obtains a range $W_B$ of the transducer 1 for receiving the transmitted wave S23 which has penetrated the second phantom 365 in a case where the ultrasound wave S21 is transmitted to the artificial second phantom 365 having the shape of the second template 364 under the same condition as when the received signal for generating the transmitted wave image 230 is received. For example, in the artificial second phantom 365, similar to the artificial phantom 381, the ultrasound attenuation rate of the inner region of the boundary 222 is a value A3 set in advance, and the ultrasound attenuation rate of the outer region of the boundary 222 is a value A4 (>A3, for example, A4 is infinite) set in advance. The range $W_B$ of the transducer 1, which has been obtained for each incident angle θ of the ultrasound wave S21, for receiving the transmitted wave S23 can be expressed in a sinogram having the array direction of the transducers 1 and the incident angle θ of the ultrasound wave S21 on the target 10 at the time of transmission as axes, for example, as in FIG. 9(g). The range $W_B$ of the transducer 1, at which the transmitted wave S23 having penetrated straight the inner side of the second phantom 365 corresponding to the shape of the boundary 222 arrives, is expressed as a belt-like region of white (in which the received signal has a predetermined value), and the range of the transducer 1, at which the transmitted wave S23 having penetrated the outer region of the second phantom 365 arrives (or no transmitted wave S23 arrives), is expressed in black (in which the received signal is zero).

The extraction unit 361 extracts the received signal of the transmitted wave S23 which has penetrated a region within the target 10 corresponding to the second phantom 365 from the actual received signal. For example, in the actual received signals expressed in the sinogram (FIG. 5(d)), the received signal of the transmitted wave S23 which has penetrated a region within the target 10 corresponding to the second phantom 365 is extracted by extracting a signal having intensity equal to or greater than a threshold value set in advance. The extracted received signal can be expressed in a sinogram as in FIG. 9(h). FIG. 9(h) illustrates a spreading width $W_Q$ of a received signal in the array direction of the transducers 1.

The second width adjustment unit 362 adjusts the spreading width $W_Q$ in the array direction of the transducers 1 for the received signal extracted by the extraction unit 361 such that the spreading width $W_Q$ coincides with the range $W_B$ of the transducer 1 for receiving the transmitted wave S23 of the second phantom 365 obtained by the second forward projection unit 360. Specifically, the second width adjustment unit 362 obtains a ratio $W_B/W_Q$ of the range $W_B$ to the range $W_Q$ for each incident angle θ of the ultrasound wave S21 and calculates an average $(W_B/W_Q)_{Ave}$ of the obtained ratio $W_B/W_Q$. The second width adjustment unit 362 performs an adjustment in which the spreading width $W_Q$ is widened or reduced to approximate the range $W_B$, by applying the obtained average $(W_B/W_Q)_{Ave}$ to the value of the range $W_Q$ of the transducers 1 in the entire belt-like region of the sinogram in FIG. 9(h). FIG. 9(j) illustrates a received signal after being adjusted by the second width adjustment unit 362.

The superimposition unit 363 extracts and eliminates a received signal of the transmitted wave S23 in a region within the target 10 corresponding to the second phantom 365 from the received signal after being adjusted by the width adjustment unit 355 (which corresponds to FIG. 5(e)). For example, the received signal of the transmitted wave S23 which has penetrated a region within the target 10 corresponding to the second phantom 365 is eliminate by extracting and eliminating a signal having intensity equal to or greater than the threshold value set in advance among the received signals after being adjusted by the width adjustment unit 355. The received signal (FIG. 9(j)) after being adjusted by the second width adjustment unit 362 is superimposed on the received signal (FIG. 9(i)) after being eliminated, thereby generating a superimposed received signal (FIG. 9(k)).

The transmitted wave image reconstruction unit 352 reconstructs a second post-adjustment transmitted wave image by performing back projection of the received signal (FIG. 9(k)) after being superimposed by the superimposition unit 363.

In this manner, the second received signal adjustment unit 359 generates a post-adjustment transmitted wave image in which not only the boundary 221 but also the boundary 222 on the inner side thereof is emphasized in the transmitted wave image 230, by adjusting the spreading width $W_Q$ of a received signal in the array direction of the transducers 1 in a region corresponding to the inner side of the boundary 222 for the actual received signal.

In this manner, the ultrasonic imaging device of Embodiment 3 can acquire a post-adjustment transmitted wave image in which all of the boundaries are clear and a post-adjustment reflected image which is obtained from the post-adjustment transmitted wave image through a computation and has clear boundaries, by sequentially performing processing of emphasizing the boundaries in the post-adjustment transmitted wave image with respect to other boundaries as well.

Embodiment 3

Hereinafter, as the present Embodiment 3, a specific ultrasonic imaging device having the configurations of both the ultrasonic imaging device of Embodiment 1 and Embodiment 2 will be described using FIG. 10 and the like. In description of the ultrasonic imaging device of Embodiment 3, configurations similar to those of the apparatuses of Embodiments 1 and 2 will not be described.

FIG. 10 is a block diagram illustrating an overall configuration of the ultrasonic imaging device of Embodiment 3. An ultrasonic imaging device 5 in FIG. 10 includes the plurality of transmission/reception units 3 which are individually connected to the transducer array 2 and control transmission and reception of an ultrasound wave in the transducer array 2, a control unit 4 which control each of the transmission/reception units 3, a storage unit 52, a display unit 53, and an operation unit (interface (I/F)) 40. Each of the transmission/reception units 3 includes the transmission unit 6 and the reception unit 7 described above and also includes a transmission/reception switch (T/R SW) 8 for switching the state between transmission and reception of the ultrasound wave. One transmission/reception unit 3 is connected to one transducer 1, and each of the transmission/reception units 3 can independently transmit and receive an ultrasound wave signal. The control unit 4 includes the image generation unit 50 having the configuration in FIG. 6 as described in Embodiments 1 and 2. In addition, the control unit 4 may perform control differently by outputting control signals S51, S52, and the like with respect to each of the transmission/reception units 3. For example, the control unit 4 inputs the control signal S51 for instructing the transmission/reception units 3 to transmit an ultrasound wave such that an ultrasound wave transmitting operation is performed. The control unit 4 inputs the control signal S52 for instructing the transmission/reception units 3 to receive an ultrasound wave such that an ultrasound wave receiving operation is performed. The storage unit 52 stores setting related to a transmitting and receiving operation of an ultrasound wave of each of the transmission/reception units 3, information of a signal waveform an electric signal S1 output to the transmission unit 6, a reflected wave image and a transmitted wave image of the target 10 obtained through image generation, and the like. The display unit 53 displays a reflected wave image and (or) a transmitted wave image which has been generated. The operation unit 40 receives an input of an image capturing condition or an image capturing starting instruction from an operator and exchanges information with other instruments.

The transmission unit 6 generates the transmission signal S11 by amplifying the electric signal S1 input from the control unit 4 to desired intensity and outputs the generated transmission signal S11 to the transducer 1. The transducer 1 has a structure including a matching layer, an acoustic lens, and the like. The transducer 1 converts the transmission signal S11 received from the transmission unit 6 into an ultrasound wave and radiates (transmits) the converted ultrasound wave. The sound pressure of the ultrasound wave signal S21 radiated from the transducer 1 changes in accordance with the signal intensity of the transmission signal S11 delivered to the transducer 1. The signal intensity of the transmission signal S11 generated by the transmission unit 6 is set by the control signal S51.

The ultrasound wave signal S21 radiated from the transducer 1 passes through a space 30 and arrives at the transducer 1 from which it is radiated and other transducers 1. The transducer 1 has a structure including the matching layer, the acoustic lens, and the like. The transducer 1 converts the arrived ultrasound wave signal S21 into the received signal S31 which is an electric signal and outputs the converted received signal S31. The reception unit 7 amplifies the electric signal (received signal S31) output by the transducer 1. The reception unit 7 reduces and quantizes noise beyond a desired frequency band, generates a post-amplification received signal S41, and outputs the generated post-amplification received signal S41 to the control unit 4.

The transmission/reception switch S disconnects the reception unit 7 and the transducer 1 from each other at the time of a transmitting operation and causes a short-circuit therebetween at the time of a receiving operation. Accordingly, the reception unit 7 is prevented from breaking due to the high-voltage transmission signal S11 output from the transmission unit 6 to the transducer 1 during a transmitting operation.

The control unit 4 has a central processing unit (CPU) (not illustrated) and a memory (not illustrated) in which a program has been stored in advance. The CPU realizes the function of the image generation unit 50 in FIG. 6 by reading and executing the program. The control unit 4 is not limited to the configuration in which the function thereof is realized by means of software executed by the CPU. A part or the entirety of the control unit 4 may be constituted of hardware, for example, a custom integrated circuit (IC) such as an application specific integrated circuit (ASIC), and a programmable IC such as a field-programmable gate array (FPGA).

Figure 11:
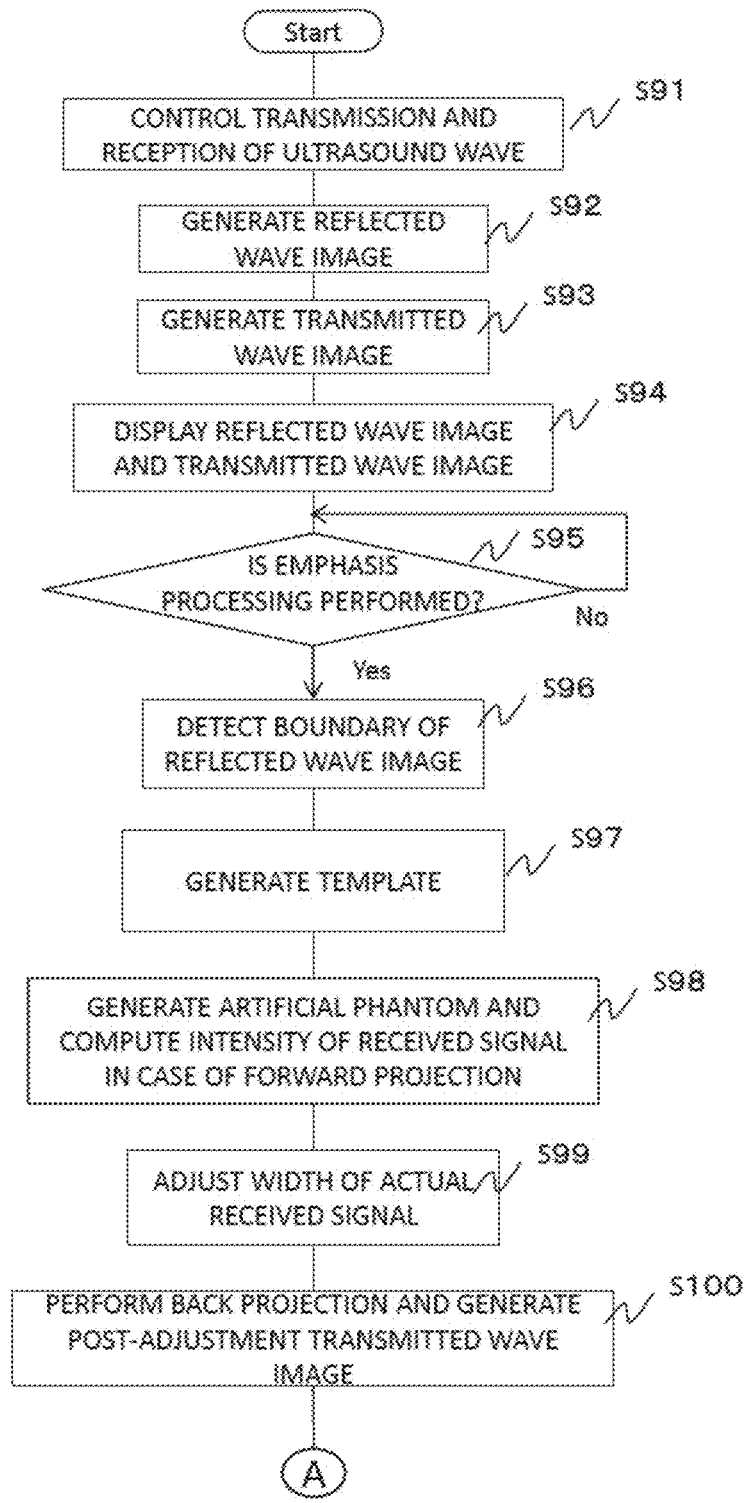
FIG. 11 is a flow chart illustrating an operation of the ultrasonic imaging device of Embodiment 3.
Figure 12:
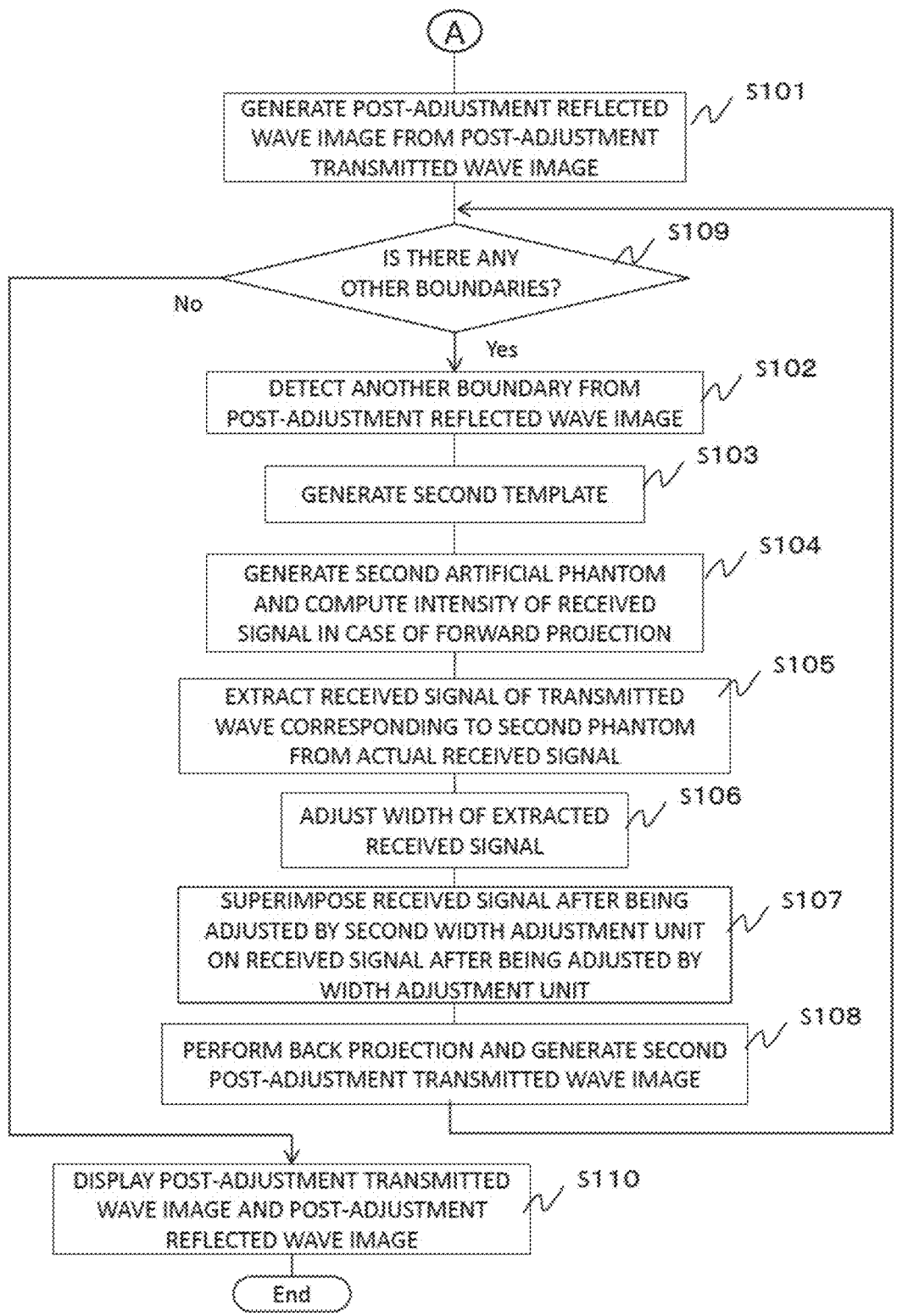
FIG. 12 is the flow chart illustrating an operation of the ultrasonic imaging device of Embodiment 3.
Figure 13:
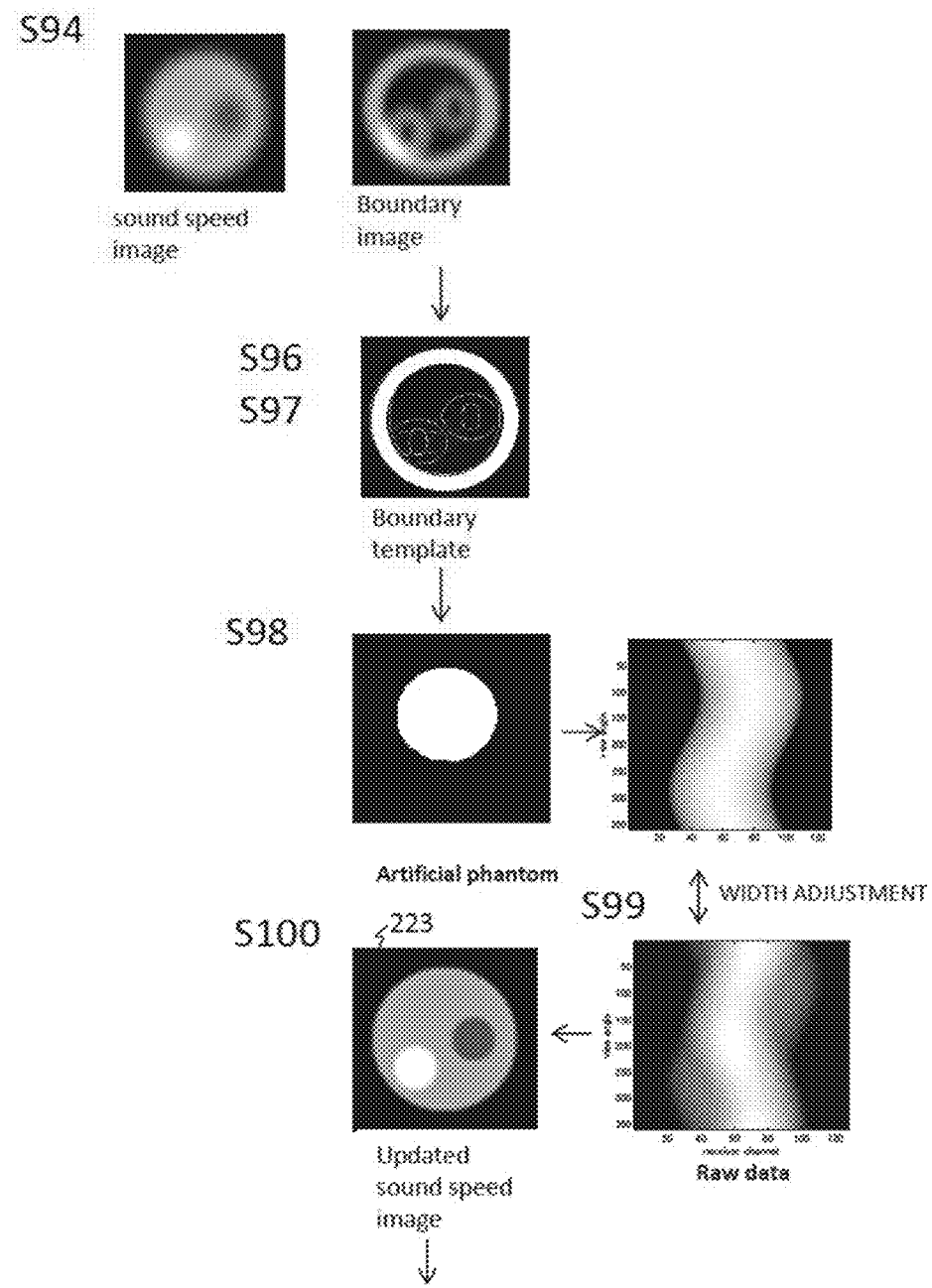
FIG. 13 is a view illustrating images acquired through operations of the ultrasonic imaging device of Embodiment 3.
Figure 14:
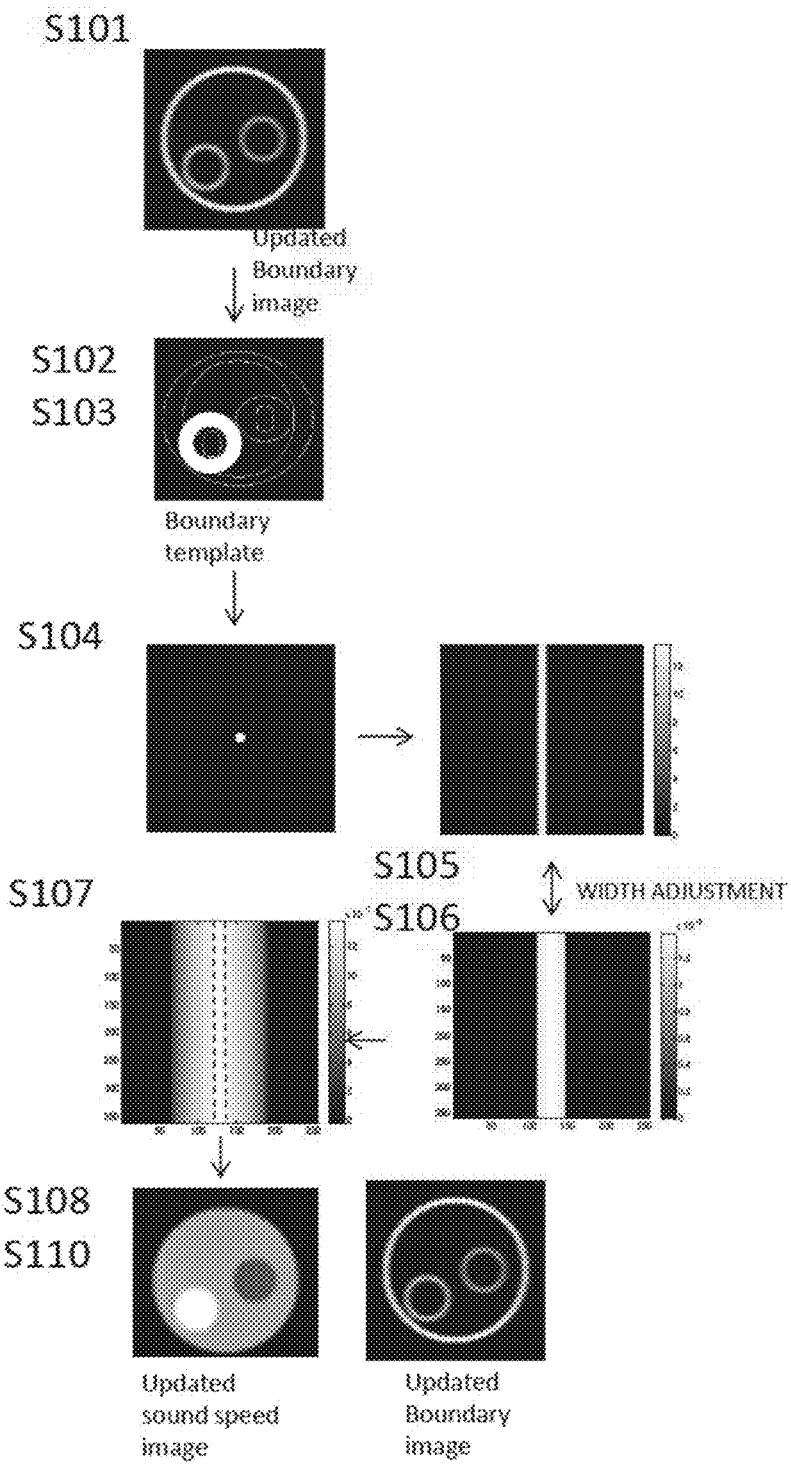
FIG. 14 is a view illustrating images acquired through operations of the ultrasonic imaging device of Embodiment 3.

Hereinafter, an operation of the control unit 4 will be described using the flow in FIGS. 11 and 12 and examples of images in FIGS. 13 and 14. The control unit 4 performs transmission and reception control of an ultrasound wave (Step S91). Specifically, the control unit 4 transmits a control signal to each of the transmission/reception units 3, so that a predetermined transmission/reception unit 3 performs a transmitting operation and all of the transmission/reception units 3 perform a receiving operation (Step S91). In accordance with this transmission and reception control, the transducer array 2 transmits the ultrasound wave signal S21 to the target 10 and receives the reflected wave S22 and for receiving the transmitted wave S23. The control unit 4 receives a received signal of the ultrasound wave from the transducer array 2.

The control unit 4 repeats the process until transmission of an ultrasound wave from all of the transducers 1 is completed while sequentially changing the transducer 1 for performing a transmitting operation. The transmission/reception unit 3 which the control unit 4 causes to perform a transmitting operation is not limited to one, and a plurality of transmission/reception units 3 may be used. The control unit 4 may cause the transducer array 2 to transmit an associated wave of an ultrasound wave by causing the plurality of transmission/reception units 3 to simultaneously perform a transmitting operation. In addition, the transducer 1 for receiving the ultrasound wave may be limited to a predetermined range in accordance with a positional relationship with the transducer 1 for transmitting an ultrasound wave.

The control unit 4 extracts the received signal of the reflected wave S22 from the received signal of the ultrasound wave and generates the reflected wave image 220 based on the received signal of the reflected wave S22 (Step S92). Specifically, the image generation unit 50 of the control unit 4 extracts the received signals in the time zone set in advance, in accordance with the positional relationship between the transducer 1 transmitting the ultrasound wave signal S21 and the transducer 1 receiving the ultrasound wave signal S21, thereby individually extracting a received signal of the transmitted wave S23 and a received signal of the reflected wave S22. Moreover, the reflected wave image generation unit 350 calculates the signal delay time which is a difference between a timing (time) at which the ultrasound wave signal S21 is transmitted and a timing (time) at which the extracted received signal of the reflected wave S22 is received. The reflected wave image generation unit 350 calculates the position of the reflection point at which the ultrasound wave signal S21 is reflected, based on the distance of the propagation path between the transducer 1 which has transmitted an ultrasound wave and the transducer 1 which has received an ultrasound wave, by applying the sound speed set in advance to the signal delay time. In addition, the amplitude of the extracted received signal of the reflected wave S22 is converted into luminance and luminance is set for the position (pixel) of the reflection point. This computation is performed with respect to all of the received signals of the reflected wave S22, so that the reflected wave image 220 is generated (Step S92). In addition, the method is not limited thereto. The reflected wave image 220 may be generated by performing phasing addition (received beam forming) of the received signal of the reflected wave S22 at a plurality of reception time focal points set in the space 30 and converting the signal intensity after phasing addition into luminance.

Next, the control unit 4 generates the transmitted wave image 230 based on the received signal of the transmitted wave S23 extracted in Step S92 (Step 393). Hereinafter, an example of generating a sound speed image (sound speed distribution image) as the transmitted wave image 230 will be described. An attenuation image (attenuation amount distribution image) may be generated together with the sound speed image, and only an attenuation image may be generated. Specifically, the transmitted wave image reconstruction unit 352 of the transmitted wave image generation unit 349 of the control unit 4 obtains the sound speed based on the distance of the propagation path in accordance with a positional relationship between the transducer 1 which has transmitted an ultrasound wave and the transducer 1 which has received an ultrasound wave, and an ultrasound wave propagation time which is a difference between a timing at which the ultrasound wave signal S21 has been transmitted and a timing at which the extracted received signal of the transmitted wave S23 is received. The transmitted wave image reconstruction unit 352 generates the transmitted wave image 230 by reconstructing the sound speed distribution image through the ultrasound tomography method based on the obtained sound speed (Step S93). More specifically, the transmitted wave image reconstruction unit 352 obtains the average sound speed of the ultrasound wave signal S21 by calculating the distance between the transducers 1 including the positional coordinates of the transducer 1 which has transmitted the ultrasound wave signal S21 and the transducer 1 which has received the transmitted wave S23 and dividing the obtained distance between the transducers 1 by the ultrasound wave propagation time. The transmitted wave image reconstruction unit 352 obtains the average sound speed at each angle in a case where the ultrasound wave signal S21 is transmitted to the target 10 at various angles, by calculating this average sound speed with respect to a combination of the transducer 1 which has transmitted the ultrasound wave signal S21 and the transducer 1 which has received the transmitted wave S23. Since the average sound speed is an average of the sound speed distributions of the paths through which the ultrasound wave signal S21 has passed (has been propagated), the sound speed distribution image of the target 10 is calculated by using computation processing of a known tomography method such as a matrix computation, such that no contradiction is caused in the average sound speed in the various paths.

In addition, as the transmitted wave image 230, in a case where an attenuation image (attenuation amount distribution image) is generated, in Step S93, the transmitted wave image reconstruction unit 352 obtains a signal attenuation amount based on the difference in the intensity between the ultrasound wave signal S21 and the received signal of the transmitted wave S23 and generates the transmitted wave image 230 by reconstructing an attenuation image through the ultrasound tomography method based on the obtained signal attenuation amount. Moreover, the transmitted wave image reconstruction unit 352 calculates the average signal attenuation amount in the propagation path from the transmitting transducer 1 to the receiving transducer 1 based on the difference in the intensity between the ultrasound wave signal S21 and the received signal of the transmitted wave S23. The average signal attenuation amount is the average of the signal attenuation amount distributions of the paths which the ultrasound wave signal S21 has penetrated. Thus, using the average signal attenuation amount in a case where the ultrasound wave signal S21 is transmitted at various angles, the signal attenuation amount distribution image of the target 10 is calculated by using computation processing of a known tomography method such as a matrix computation.

Figure 15:
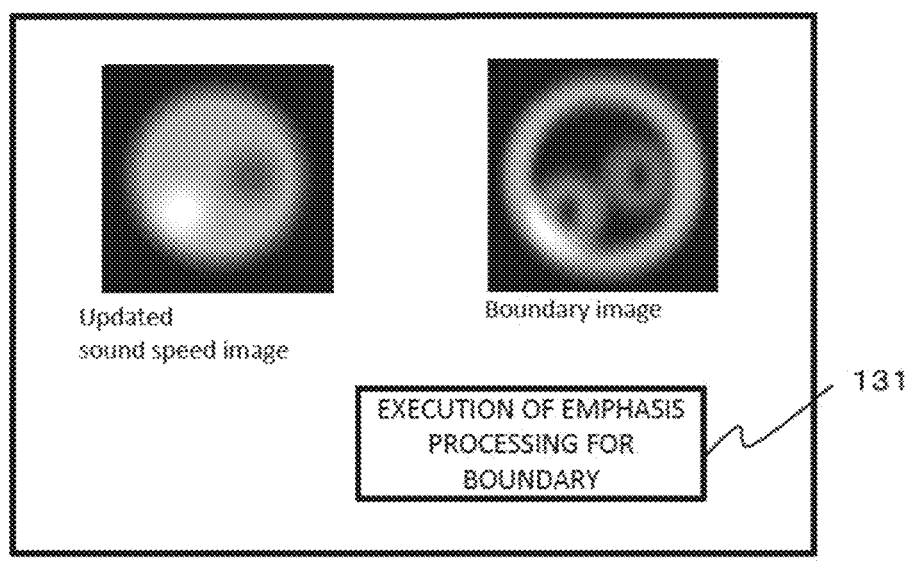
FIG. 15 is a view illustrating an example of a display screen of the ultrasonic imaging device of Embodiment 3.

The reflected wave image generation unit 350 and the transmitted wave image generation unit 349 of the control unit 4 transmit the reflected wave image 220 and the transmitted wave image 230 (sound speed distribution image) of the target 10, which have been generated, to the display unit 53, so that the display unit 53 displays a screen including the reflected wave image 220 and the transmitted wave image 230 (Step S94). FIG. 15 is a view illustrating an example of a display screen of the ultrasonic imaging device, that is, an example of a screen including the reflected wave image 220 and the transmitted wave image 230. In FIG. 15, as an example of the transmitted wave image 230, only the sound speed distribution image is displayed. However, in a case where the attenuation amount distribution image is also generated as the transmitted wave image 230, the attenuation amount distribution image may be displayed together with the sound speed distribution image as the transmitted wave image 230, or only the attenuation amount distribution image may be displayed.

The control unit 4 determines whether or not emphasis processing of the boundary is performed (Step S95). Specifically, the control unit 4 determines whether or not an object 131, such as a button or an icon for instructing "execution of emphasis processing for a boundary" via the operation unit 40, is pressed by an operator that has seen the display of the display unit 53. If the object 131 is pressed (Yes in Step S95), the following processing is performed.

First, the reflected wave image boundary detection unit 351 of the control unit 4 detects a boundary from the reflected wave image 220 generated in Step S92 (Step S96). For example, as the boundary, the reflected wave image boundary detection unit 351 detects a pixel within the reflected wave image 220 of which luminance is higher than a predetermined threshold value through binary coded processing. The boundary need only be able to be detected through image processing. The boundary may be detected by performing mask processing or filter processing with respect to the reflected wave image 220.

The boundary template generation unit 380 of the control unit 4 generates the template 356 corresponding to the shape of the outside boundary 221 detected by the reflected wave image boundary detection unit 351 and transmits the template 356 to the transmitted wave image generation unit 349 (Step S97). For example, the boundary template generation unit 380 may extract the boundary by comparing the closed areas of regions formed by the detected boundaries or comparing the luminance of the boundaries. The method does not matter.

The forward projection unit 354 of the transmitted wave image generation unit 349 generates the artificial phantom 381 having the shape of the template 356 based on the received template 356 and obtains the intensity of the received signal acquired in a case where the phantom 381 is subjected to forward projection in the transducer array 2, through a computation. Moreover, the range $W_A$ of the transducer 1 which is a spreading width in the sinogram having the obtained intensity of the received signal is obtained (Step S98).

The width adjustment unit 355 of the control unit 4 adjusts the spreading width $W_R$ in the sinogram having the intensity of the actual received signal such that the spreading width $W_R$ approximates the range $W_A$ of the transducer 1 obtained by the forward projection unit 354 (Step S99).

The transmitted wave image reconstruction unit 352 of the control unit 4 reconstructs (generates) the post-adjustment transmitted wave image 233 by performing back projection of the received signal after being adjusted by the width adjustment unit 355 and transmits the reconstructed post-adjustment transmitted wave image 233 to the reflected wave image generation unit 350 (Step S100). Accordingly, the transmitted wave image reconstruction unit 352 generates the post-adjustment transmitted wave image 233 in which the boundary 231 corresponding to the boundary 221 of the reflected wave image 220 is emphasized in the transmitted wave image 230.

Next, the post-adjustment reflected wave image generation unit 357 of the control unit 4 generates the post-adjustment reflected wave image 223 acquired in a case where the distribution of ultrasound penetration characteristics (sound speed $c_{variable}$) indicated in the transmitted post-adjustment transmitted wave image 233 is irradiated with the ultrasound wave signal S21 (Step S101).

The second boundary detection unit 358 of the control unit 4 determines whether or not there are any other boundaries to be subjected to emphasis processing in the post-adjustment reflected wave image 223 (Step S109). Specifically, the second boundary detection unit 358 determines whether or not a boundary other than the boundary 221 corresponding to the boundary 231 is detected in the post-adjustment reflected wave image 223. In a case where a boundary is detected (Yes in Step S109), the control unit 4 performs the following processing.

The second boundary detection unit 358 of the control unit 4 detects the second boundary 222 which is another boundary positioned on the inner side of the boundary 221 in the post-adjustment reflected wave image 223 (Step S102).

The boundary template generation unit 380 of the control unit 4 generates the second template 364 corresponding to the second shape of the boundary 222 and transmits the second template 364 to the transmitted wave image generation unit 349 (Step S103). The second forward projection unit 360 of the control unit 4 generates the second artificial phantom 365 having the shape of the second template 364 and obtains the intensity of the received signal acquired in a case where the second phantom 365 is subjected to forward projection in the transducer array 2, through a computation. Moreover, the range $W_B$ of the transducer 1 which is a spreading width in the sinogram having the obtained intensity of the received signal is obtained (Step S104).

Based on the actual received signal, the extraction unit 361 of the control unit 4 extracts the received signal of the transmitted wave S23 which has penetrated a region within the target 10 corresponding to the second phantom 365, for example, in the sinogram (Step S105).

The second width adjustment unit 362 of the control unit 4 adjusts the spreading width $W_Q$ in the sinogram of the actual received signal such that the spreading width $W_Q$ coincides with the range $W_B$ of the transducer 1 for receiving the transmitted wave S23 of the second phantom 365 obtained by the second forward projection unit 360 (Step S106).

The super imposition unit 363 of the control unit 4 extracts and eliminates the received signal corresponding to the second phantom 365 from the received signal after being adjusted by the width adjustment unit 355 in Step S99 and superimposes the received signal after being adjusted by the second width adjustment unit 362 on the received signal after being eliminated (Step S107).

The transmitted wave image reconstruction unit 352 reconstructs (generates) the second post-adjustment transmitted wave image by performing back projection of the received signal after being superimposed (Step S108).

The control unit 4 returns to Step S109, and the second boundary detection unit 358 of the control unit 4 determines whether there are any other boundaries to be subjected to emphasis processing in the post-adjustment reflected wave image 223. In a case where there still remains a boundary to be subjected to emphasis processing in the post-adjustment reflected wave image 223 (Yes in Step S109), the control unit 4 repeats Steps S102 to S108. If emphasis processing of all of the boundaries ends (No in Step S109), the control unit 4 causes the display unit 53 to display the post-adjustment transmitted wave image and the post-adjustment reflected wave image which are generated at the end (Step S110). The control unit 4 may determine whether or not emphasis processing has ended with respect to all of the boundaries based on an image processing result or may determine the same by receiving pointing-out of the non-processed boundary from an operator.

In Step S96, the reflected wave image boundary detection unit 351 may detect a plurality of boundaries. In Step S97, the boundary template generation unit 380 may generate the template 356 corresponding to only the outside boundary and may generate the template 356 corresponding to a plurality of boundaries. In a case where the template 356 corresponding to a plurality of boundaries is generated, in Step S98, the forward projection unit 354 generates the phantom 381 based on the outside boundary among the boundaries within the template 356.

In addition, in Step S96, the reflected wave image boundary detection unit 351 may detect only the outside boundary.

Since the outside boundary which is a boundary between water and the target 10 has a clearer shape of the contour of the boundary than the inside boundary which is a boundary between tissues receiving an influence such as scattering within the target 10 and the boundary is likely to be detected, it is preferable that the phantom 381 generated based on the outside boundary in Step S98. The phantom 381 may foe generated based on the inside boundary in Step S98.

In this manner, in the present embodiment, in the image generation unit 50, the boundary of a transmitted wave image generated by the transmitted wave image generation unit 349 is emphasized based on the boundary detected by using a reflected wave image generate by the reflected wave image generation unit 350. Moreover, a reflected wave image having an emphasized boundary is generated from a transmitted wave image after being emphasized.

Figure 16:
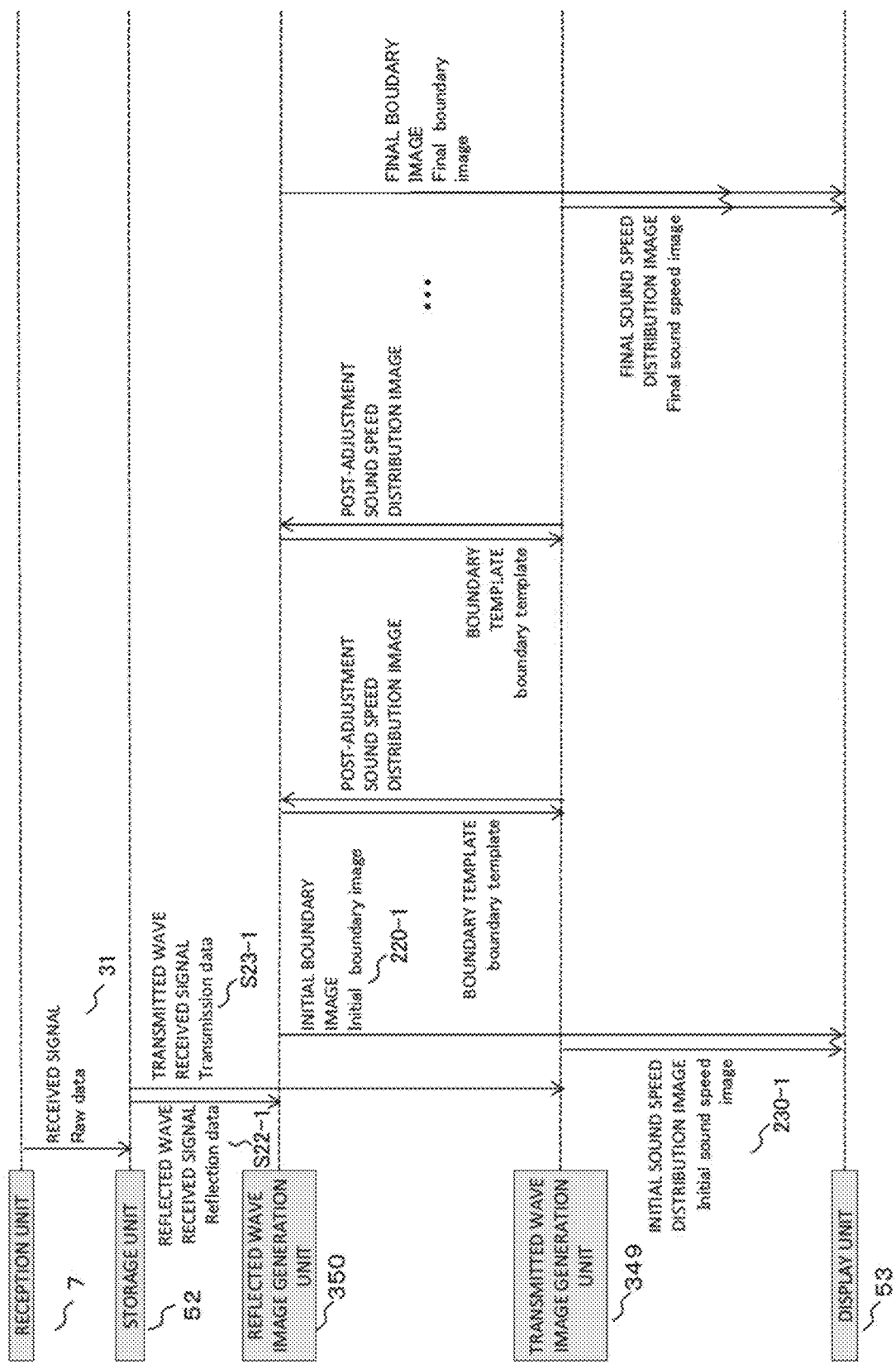
FIG. 16 is a sequence diagram illustrating a flow of a signal of the ultrasonic imaging device of Embodiment 3.

FIG. 16 is a sequence diagram illustrating a flow of a signal of the ultrasonic imaging device. An example in which the transmitted wave image is a sound speed distribution image will be described. When the reception unit 7 receives the received signal S31 (raw data) from the transducer 1, the received signal S31 is stored in the storage unit 52 via the image generation unit 50. The reflected wave image generation unit 350 acquires a received signal S22-1 of the reflected wave S22 among the received signals S31 from the storage unit 52, generates a reflected wave image, and transmits the generated reflected wave image to the display unit 53 as an initial boundary image 220-1. In addition, the transmitted wave image generation unit 349 acquires a received signal S23-1 of the transmitted wave S23 among the received signals S31 from the storage unit 52, generates a transmitted wave image, and transmits the generated transmitted wave image to the display unit 53 as an initial sound speed distribution image 230-1.

The reflected wave image generation unit 350 detects the boundary in the initial boundary image 220-1, generates a boundary template 356-1, and transmits the generated boundary template 356-1 to the transmitted wave image generation unit 349. The transmitted wave image generation unit 349 generates a sound speed template 381-1 (artificial phantom) based on the received boundary template 356-1, generates a post-adjustment sound speed distribution image 233-1 in which the boundary is emphasized based on the generated sound speed template and the initial sound speed distribution image 230-1, and transmits the generated post-adjustment sound speed distribution image 233-1 to the reflected wave image generation unit 350.

The reflected wave image generation unit 350 emphasizes the boundary of the initial boundary image 220-1 based on the received post-adjustment sound speed distribution image 233-1, generate a boundary template 356-2 again, and transmits the boundary template 356-2 having the emphasized boundary to the transmitted wave image generation unit 349. The transmitted wave image generation unit 349 generates a post-adjustment sound speed distribution image 233-2 again based on the received boundary template 356-2 having the emphasized boundary, and the post-adjustment sound speed distribution image 233-1 and transmits the generated post-adjustment sound speed distribution image 233-2 to the reflected wave image generation unit 350. The reflected wave image generation unit 350 further emphasizes the boundary which has been previously emphasized based on the received post-adjustment sound speed distribution image 233-2, generates a boundary template 356-3 again, and transmits the generated boundary template 356-3 to the transmitted wave image generation unit 349.

The above-described processing is repeated a predetermined number of times, and the reflected wave image generation unit 350 and the transmitted wave image generation unit 349 transmit a boundary image generated at the end, a sound speed image, and an attenuation image to the display unit 53.

In this manner, the same boundaries are repetitively emphasized while reciprocating between the transmitted wave image generation unit 349 and the reflected wave image generation unit 350 in the processing. Accordingly, it is possible to generate a transmitted wave image and a reflected wave image in which the boundary is emphasized with high accuracy, in a short time. In addition, the different boundaries are repetitively emphasized while reciprocating therebetween in the processing. Accordingly, it is possible to generate a transmitted wave image and a reflected wave image in which all of the boundaries are emphasized with high accuracy, in a short time.

Figure 17:
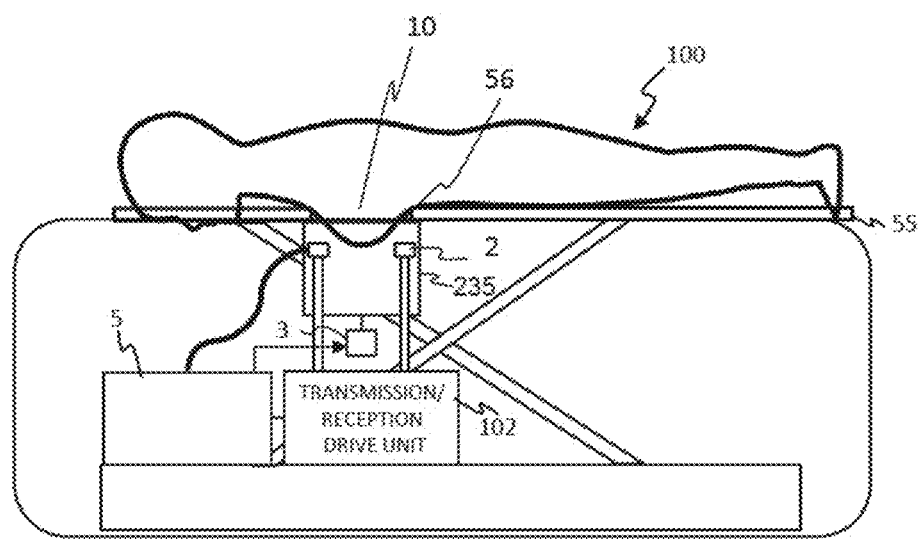
FIG. 17 is a side view illustrating a configuration of a mammographic apparatus of Embodiment 3.

It is possible to constitute a mammographic apparatus as illustrated in FIG. 17 using the ultrasonic imaging device described in the present embodiment. The mammographic apparatus in FIG. 17 includes a transmission/reception drive unit 102 in which an opening 56 is provided in a bed 55, the water tank 235 is disposed below the opening 56, and the transducer array 2 vertically moves inside the water tank 235. Since an image of breasts can be easily captured by using the mammographic apparatus having such a configuration, it is possible for an operator herself to perform self-image capturing.

In the embodiments described above, as the method of emphasizing the boundary of the transmitted wave image, a method in which the width of the transducer (the width of the sinogram) for receiving a received signal is adjusted and the received signal is subjected to back projection is used. However, the present invention is not limited to the method, and a different method may be used.

Figure 18A:
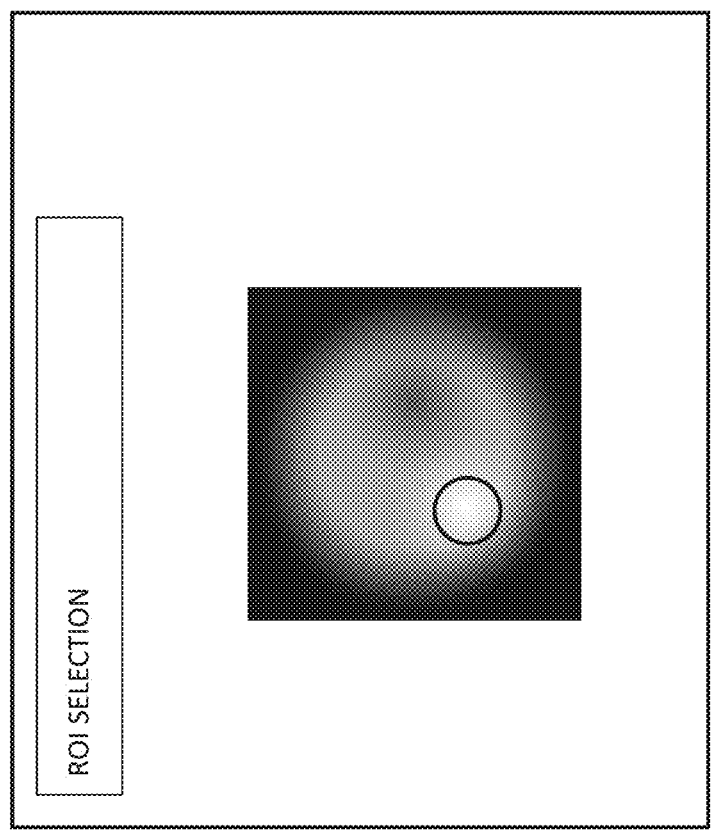
FIGS. 18A and 18B are views illustrating examples of a registration screen of another embodiment.
Figure 18B:
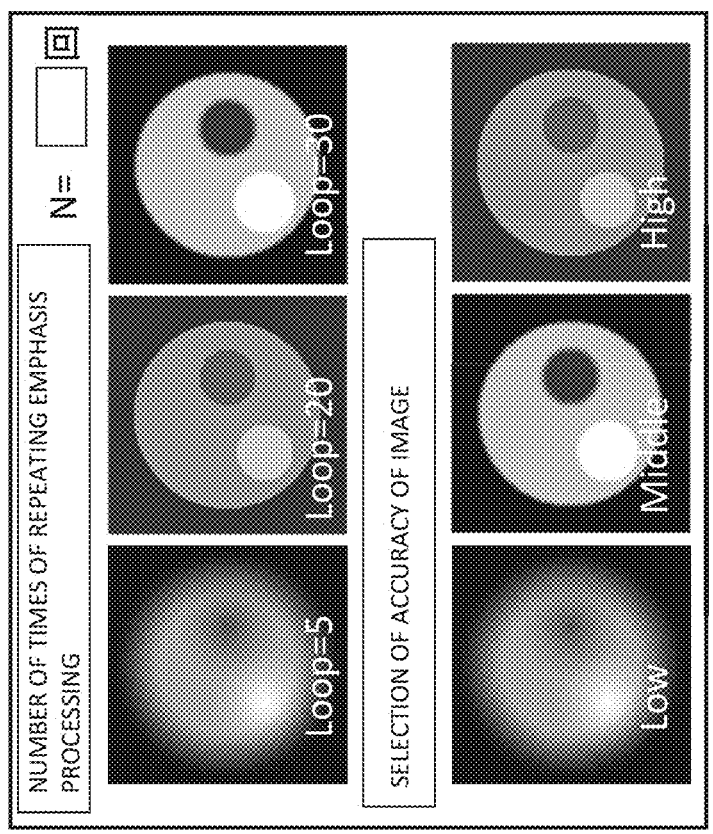

For example, the image generation unit 50 may use a method in which at least one of size adjustment processing and gradation emphasis processing of an image (boundary 231) corresponding to the boundary 221 is performed with respect to the transmitted wave image, such that the size of the image (boundary 231) corresponding to the boundary 221 in the transmitted wave image coincides therewith, while having the shape of the boundary 221 of the target 10 detected from the reflected wave image as the template. In this method, since emphasis processing is repeated, the emphasis degree of the boundary 231 can be gradually increased. For example, as illustrated in FIG. 18(a) as an example of a screen, the control unit 4 receives selection of ROI, which is a boundary to be emphasized, on the transmitted wave image from an operator via the display unit 53 or the I/F 40. Thereafter, as illustrated in FIG. 18(b), the control unit 4 receives selection of the number of times N of repeating emphasis processing or the degree of accuracy of an image after emphasis processing from the operator via the display unit 53 or the I/F 40. The control unit 4 repeats the emphasis processing until reaching the number of times N or the degree which has been received. In this method as well, the processing of calculating a reflected wave image from the transmitted wave image after emphasis processing through a computation is performed similar to that in the embodiment described above.

INDUSTRIAL APPLICABILITY

The present invention can be applied to an ultrasonic imaging device including a plurality of transducers.

REFERENCE SIGNS LIST

1 TRANSDUCER
2 TRANSDUCER ARRAY
3 TRANSMISSION/RECEPTION UNIT
4 CONTROL UNIT
5 ULTRASONIC IMAGING DEVICE
6 TRANSMISSION UNIT
7 RECEPTION UNIT
8 TRANSMISSION/RECEPTION SWITCH
52 STORAGE UNIT
50 IMAGE GENERATION UNIT
53 DISPLAY UNIT
349 TRANSMITTED WAVE IMAGE
350 REFLECTED SAVE IMAGE GENERATION UNIT

The invention claimed is:

1. An ultrasonic imaging device comprising:
a transducer array in which a plurality of transducers transmitting and receiving an ultrasound wave are arrayed;
a transmitter which transmits an electric signal to at least one of the plurality of transducers, such that the transmitted electric signal is converted into an ultrasound wave and the ultrasound wave is transmitted to a target;
a receiver which receives a received signal that is an electric signal output by each of the plurality of transducers having received a reflected wave and a transmitted wave of the ultrasound wave of the target; and
a processor programmed to individually generate a reflected wave image of a cross section of the target using the reflected wave and a transmitted wave image of the cross section of the target using the transmitted wave,
wherein the processor detects a boundary of the target in the reflected wave image, and the processor generates the transmitted wave image such that a boundary in the transmitted wave image corresponding to the boundary detected in the reflected wave image is emphasized,
wherein the transmitter transmits the ultrasound wave having a predetermined spreading angle a plurality of times while changing a position of the transducer for transmitting the ultrasound wave so as to change an incident angle of the ultrasound wave on the target,
wherein the receiver receives the transmitted wave of the ultrasound wave of the target every time when the ultrasound wave is transmitted,
wherein the processor is programed to perform back projection of the received signal output by the plurality of transducers in a space where the target is disposed every time the ultrasound wave is transmitted and reconstruct the transmitted wave image, and perform processing of the received signal and emphasize an image of the boundary in the reconstructed transmitted wave image,
wherein the processor is programmed to generate a template corresponding to a shape of the boundary in the reconstructed transmitted wave image,
wherein the processor is programmed to generate an artificial phantom having a shape of the template in the transducer array and obtain a range of the transducer for receiving a transmitted wave which has penetrated the artificial phantom in a case where an ultrasound wave is artificially transmitted to the artificial phantom under the same condition as when the received signal for generating the transmitted wave image is received,
wherein the processor is programmed to adjust the received signal such that a spreading width of the received signal in an array direction of the transducers obtained from the template corresponding to the shape of the boundary is set equal to the range of the transducer,
wherein the processor adjusts a sinogram of the received signal such that the spreading width of the received signal in the array direction of the transducers is set equal to the range of the transducer for receiving the transmitted wave which has penetrated the artificial phantom, wherein a first axis of the sinogram is the array direction of the transducers and a second axis of the sinogram is the incident angle of the ultrasound wave on the target at the time of transmission, and
wherein the processor performs the back projection of the received signal after being adjusted and reconstructs a post-adjustment transmitted wave image.

2. The ultrasonic imaging device according to claim 1, wherein the processor widens or reduces the spreading width of the received signal in the array direction of the transducers in the sinogram so that the spreading width thereof is set equal to the range of the transducer for receiving the transmitted wave of the artificial phantom.

3. The ultrasonic imaging device according to claim 1, wherein the processor is further programmed to:
perform a computation to generate a post-adjustment reflected wave image acquired in a case where the ultrasound wave is transmitted to the artificial phantom having ultrasound penetration characteristics corresponding to that of the post-adjustment transmitted wave image and a reflected wave thereof is received, using the post-adjustment transmitted wave image generated by the processor using the received signal after being adjusted;
detect a first boundary in the post-adjustment reflected wave image and further detect a second boundary positioned within the first boundary; and
adjust the post-adjustment transmitted wave image such that the second boundary in the post-adjustment transmitted wave image is emphasized.

4. The ultrasonic imaging device according to claim 3, wherein the processor generates the post-adjustment reflected wave image considering that the ultrasound wave is refracted in accordance with a difference of ultrasound penetration characteristics in a boundary of a region having different ultrasound penetration characteristics in the target having ultrasound penetration characteristics corresponding to that of the post-adjustment transmitted wave image.

5. The ultrasonic imaging device according to claim 3, wherein the processor generates a second template corresponding to a shape of the second boundary,
wherein the processor is further programmed to:
generate an artificial second phantom having a shape of the second template in a case where the ultrasound wave is transmitted to the artificial second phantom under the same condition as when the received signal for generating the transmitted wave image is received,
perform forward projection on the artificial second phantom and obtain a range of the transducer for receiving the transmitted wave which has penetrated the artificial second phantom,
extract the received signal of the transmitted wave which has penetrated a region within the target corresponding to the artificial second phantom,
adjust the received signal such that the spreading width of the received signal in the array direction of the transducers is set equal to the range of the transducer for receiving the transmitted wave of the artificial second phantom, and
extract and eliminate the received signal of the transmitted wave in the region within the target corresponding to the artificial second phantom after being adjusted and superimpose the received signal after being adjusted on the received signal after being eliminated, and
wherein the processor performs the back projection of the received signal after being superimposed and reconstructs a second post-adjustment transmitted wave image.

6. The ultrasonic imaging device according to claim 1, wherein the transducer array has a ring shape and is disposed to surround the target.

7. The ultrasonic imaging device according to claim 1, wherein the transmitted wave image is a distribution image of sound speeds within the target or a distribution image of ultrasound attenuation rates within the target.

8. An imaging method using an ultrasonic imaging device, the method comprising:
- delivering an electric signal to at least one of a plurality of transducers in a transducer array, such that the delivered electric signal is converted into an ultrasound wave, and the ultrasound wave is transmitted to a target;
- receiving a received signal that is an electric signal output by each of the plurality of transducers having received a reflected wave and a transmitted wave of the ultrasound wave of the target;
- individually generating a reflected wave image of a cross section of the target using the reflected wave and a transmitted wave image of the cross section of the target using the transmitted wave;
- detecting a boundary of the target in the reflected wave image and performing processing of the transmitted wave image such that a boundary in the transmitted wave image corresponding to the detected boundary is emphasized;
- wherein the ultrasound wave having a predetermined spreading angle is transmitted a plurality of times while changing a position of the transducer for transmitting the ultrasound wave so as to change an incident angle of the ultrasound wave on the target;
- wherein the transmitted wave of the ultrasound wave of the target is received every time when the ultrasound wave is transmitted;
- performing back projection of the received signal output by the plurality of transducers in a space where the target is disposed every time the ultrasound wave is transmitted and reconstructing the transmitted wave image, and performing processing of the received signal and emphasizing an image of the boundary in the reconstructed transmitted wave image;
- generating a template corresponding to a shape of the boundary in the reconstructed transmitted wave image;
- generating an artificial phantom having the shape of the template in the transducer array and obtaining a range of the transducer for receiving a transmitted wave which has penetrated the artificial phantom in a case where an ultrasound wave is artificially transmitted to the artificial phantom under the same condition as when the received signal for generating the transmitted wave image is received;
- adjusting the received signal such that a spreading width of the received signal in an array direction of the transducers obtained from the template corresponding to the shape of the boundary is set equal to the range of the transducer;
- adjusting a sinogram of the received signal such that the spreading width of the received signal in the array direction of the transducers is set equal to the range of the transducer for receiving the transmitted wave which has penetrated the artificial phantom, wherein a first axis of the sinogram is the array direction of the transducers and a second axis of the sinogram is the incident angle of the ultrasound wave on the target at the time of transmission;
- wherein the back projection of the received signal is performed after being adjusted; and
- reconstructing a post-adjustment transmitted wave image.

* * * * *